US010790044B2

(12) United States Patent
Semenyuk

(10) Patent No.: US 10,790,044 B2
(45) Date of Patent: Sep. 29, 2020

(54) SYSTEMS AND METHODS FOR SEQUENCE ENCODING, STORAGE, AND COMPRESSION

(71) Applicant: Seven Bridges Genomics Inc., Cambridge, MA (US)

(72) Inventor: Vladimir Semenyuk, Monterey, CA (US)

(73) Assignee: SEVEN BRIDGES GENOMICS INC., Cambridge, MA (US)

( * ) Notice: Subject to any disclaimer, the term of this patent is extended or adjusted under 35 U.S.C. 154(b) by 417 days.

(21) Appl. No.: 15/597,464

(22) Filed: May 17, 2017

(65) Prior Publication Data

US 2018/0089369 A1    Mar. 29, 2018

Related U.S. Application Data

(60) Provisional application No. 62/338,706, filed on May 19, 2016, provisional application No. 62/400,388, (Continued)

(51) Int. Cl.
*G16B 50/50* (2019.01)
*G06F 16/901* (2019.01)
(Continued)

(52) U.S. Cl.
CPC ............ *G16B 50/50* (2019.02); *G06F 3/0608* (2013.01); *G06F 16/9024* (2019.01); *H03M 7/40* (2013.01)

(58) Field of Classification Search
None
See application file for complete search history.

(56) References Cited

U.S. PATENT DOCUMENTS 5,298,895 A * 3/1994 Van Maren ......... H03M 7/3088
341/51
5,410,671 A * 4/1995 Elgamal ................. G06T 9/005
711/202
(Continued)

FOREIGN PATENT DOCUMENTS

WO    WO-9901940 A1 *  1/1999  ............. H03M 7/30
WO      2012096579 A3    7/2012
(Continued)

OTHER PUBLICATIONS

Agarwal, 2013, SINNET: Social interaction Network Extractor from Text, Proc IJCNLP 33-36.
(Continued)

*Primary Examiner* — Soren Harward
(74) *Attorney, Agent, or Firm* — Morgan, Lewis & Bockius LLP

(57) ABSTRACT

Genomic data is written to disk in a compact format by dividing the data into segments and encoding each segment with the smallest number of bits per character necessary for whatever alphabet of characters appears in that segment. A computer system dynamically chooses the segment boundaries for maximum space savings. A first one of the segments may use a different number of bits per character than a second one of the segments. In one embodiment, dividing the data into segments comprises scanning the data and keeping track of a number of unique characters, noting positions in the sequence where the number increases to a power of two, calculating a compression that would be obtained by dividing the genomic data into one of the plurality of segments at ones of the noted positions, and dividing the genomic data into the plurality of segments at the positions that yield the best compression.

7 Claims, 21 Drawing Sheets

Specification includes a Sequence Listing.

Related U.S. Application Data filed on Sep. 27, 2016, provisional application No. 62/400,411, filed on Sep. 27, 2016, provisional application No. 62/400,123, filed on Sep. 27, 2016.

(51) Int. Cl.
*G06F 3/06* (2006.01)
*H03M 7/40* (2006.01)

(56) References Cited

U.S. PATENT DOCUMENTS

| | | | |
|---|---|---|---|
| 5,511,158 | A | 4/1996 | Sims |
| 5,608,396 | A * | 3/1997 | Cheng .................. G06T 9/005 341/106 |
| 5,701,256 | A | 12/1997 | Marr et al. |
| 5,870,036 | A * | 2/1999 | Franaszek .......... H03M 7/3086 341/51 |
| 6,054,278 | A | 4/2000 | Dodge et al. |
| 6,223,128 | B1 | 4/2001 | Allex et al. |
| 7,577,554 | B2 | 8/2009 | Lystad et al. |
| 7,580,918 | B2 | 8/2009 | Chang et al. |
| 7,809,509 | B2 | 10/2010 | Milosavljevic |
| 7,885,840 | B2 | 2/2011 | Sadiq et al. |
| 7,917,302 | B2 | 3/2011 | Rognes |
| 8,209,130 | B1 | 6/2012 | Kennedy et al. |
| 8,340,914 | B2 | 12/2012 | Gatewood et al. |
| 8,370,079 | B2 | 2/2013 | Sorenson et al. |
| 8,639,847 | B2 | 1/2014 | Blaszczak et al. |
| 9,063,914 | B2 | 6/2015 | Kural et al. |
| 9,092,402 | B2 | 7/2015 | Kural et al. |
| 9,116,866 | B2 | 8/2015 | Kural |
| 9,390,226 | B2 | 7/2016 | Kural |
| 9,817,944 | B2 | 11/2017 | Kural |
| 2004/0023209 | A1 | 2/2004 | Jonasson |
| 2004/0153255 | A1 * | 8/2004 | Ahn .................. G16B 30/00 702/20 |
| 2005/0089906 | A1 | 4/2005 | Furuta et al. |
| 2006/0273934 | A1 * | 12/2006 | Delfs .................. H03M 7/30 341/50 |
| 2006/0292611 | A1 | 12/2006 | Berka et al. |
| 2007/0166707 | A1 | 7/2007 | Schadt et al. |
| 2008/0077607 | A1 | 3/2008 | Gatawood et al. |
| 2008/0294403 | A1 | 11/2008 | Zhu et al. |
| 2009/0119313 | A1 | 5/2009 | Pearce |
| 2009/0164135 | A1 | 6/2009 | Brodzik et al. |
| 2009/0292699 | A1 * | 11/2009 | Knowles .......... H03M 7/3086 |
| 2009/0298702 | A1 * | 12/2009 | Su .................. G16B 30/00 506/8 |
| 2009/0300781 | A1 | 12/2009 | Bancroft et al. |
| 2010/0041048 | A1 | 2/2010 | Diehl et al. |
| 2010/0169026 | A1 | 7/2010 | Sorenson et al. |
| 2011/0004413 | A1 | 1/2011 | Carnevali et al. |
| 2011/0098193 | A1 | 4/2011 | Kingsmore et al. |
| 2012/0041727 | A1 | 2/2012 | Mishra et al. |
| 2012/0045771 | A1 | 2/2012 | Beier et al. |
| 2012/0239706 | A1 | 9/2012 | Steinfadt |
| 2012/0330566 | A1 | 12/2012 | Chaisson |
| 2013/0031092 | A1 * | 1/2013 | Bhola .................. H03M 7/46 707/737 |
| 2013/0059738 | A1 | 3/2013 | Leamon et al. |
| 2013/0059740 | A1 | 3/2013 | Drmanac et al. |
| 2013/0073214 | A1 | 3/2013 | Hyland et al. |
| 2013/0124100 | A1 | 5/2013 | Drmanac et al. |
| 2013/0289099 | A1 | 10/2013 | Goff et al. |
| 2013/0311106 | A1 | 11/2013 | White et al. |
| 2014/0025312 | A1 | 1/2014 | Chin et al. |
| 2014/0051588 | A9 | 2/2014 | Drmanac et al. |
| 2014/0066317 | A1 | 3/2014 | Talasaz |
| 2014/0136120 | A1 | 5/2014 | Colwell et al. |
| 2014/0200147 | A1 | 7/2014 | Bartha et al. |
| 2014/0278590 | A1 | 9/2014 | Abbassi et al. |
| 2014/0280360 | A1 | 9/2014 | Webber et al. |
| 2014/0323320 | A1 | 10/2014 | Jia et al. |
| 2015/0056613 | A1 | 2/2015 | Kural |
| 2015/0057946 | A1 | 2/2015 | Kural |
| 2015/0094212 | A1 | 4/2015 | Gottimukkala et al. |
| 2015/0110754 | A1 | 4/2015 | Bai et al. |
| 2015/0112602 | A1 | 4/2015 | Kural et al. |
| 2015/0112658 | A1 | 4/2015 | Kural et al. |
| 2015/0197815 | A1 | 7/2015 | Kural |
| 2015/0199472 | A1 | 7/2015 | Kural |
| 2015/0199473 | A1 | 7/2015 | Kural |
| 2015/0199474 | A1 | 7/2015 | Kural |
| 2015/0199475 | A1 | 7/2015 | Kural |
| 2015/0227685 | A1 | 8/2015 | Kural |
| 2015/0293994 | A1 | 10/2015 | Kelly |
| 2015/0302145 | A1 | 10/2015 | Kural et al. |
| 2015/0310167 | A1 | 10/2015 | Kural et al. |
| 2015/0344970 | A1 | 12/2015 | Vogelstein et al. |
| 2015/0347678 | A1 | 12/2015 | Kural |
| 2015/0356147 | A1 | 12/2015 | Mishra et al. |
| 2016/0259880 | A1 | 9/2016 | Semenyuk |
| 2016/0306921 | A1 | 10/2016 | Kural |
| 2016/0364523 | A1 | 12/2016 | Locke et al. |
| 2017/0058320 | A1 | 3/2017 | Locke et al. |
| 2017/0058341 | A1 | 3/2017 | Locke et al. |
| 2017/0058365 | A1 | 3/2017 | Locke et al. |
| 2017/0198351 | A1 | 7/2017 | Lee et al. |
| 2017/0199959 | A1 | 7/2017 | Locke |
| 2017/0199960 | A1 | 7/2017 | Ghose et al. |
| 2017/0242958 | A1 | 8/2017 | Brown |

FOREIGN PATENT DOCUMENTS

| | | |
|---|---|---|
| WO | 2012098515 A1 | 7/2012 |
| WO | 2012142531 A2 | 10/2012 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Aguiar, 2012, HapCompass: A fast cycle basis algorithm for accurate haplotype assembly of sequence data, J Comp Biol 19(6):577-590.

Aguiar, 2013, Haplotype assembly in polyploid genomes and identical by descent shared tracts, BioInformatics 29(13): i352-i360.

Airoldi, 2008, Mixed membership stochastic blockmodels, JMLR 9:1981-2014.

Albers, 2011, Dindel: Accurate indel calls from short-read data, Genome Research 21:961-973.

Alioto et al., A comprehensive assessment of somatic mutation detection in cancer using whole-genome sequencing, Nature Communications, Dec. 9, 2015.

Altera, 2007, Implementation of the Smith-Waterman algorithm on reconfigurable supercomputing platform, White Paper ver 1.0 (18 pages).

Altschul, 1986, Optimal Sequence Alignment Using Affine Gap Costs, Bull Math Biol 48(5/6):603-616.

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioinformatics 29 (10):1250-1259.

Barbieri, 2013, Exome sequencing identifies recurrent SPOP, FOXA1 and MED12 mutations in prostate cancer, Nature Genetics 44:6 685-689.

Beerenwinkel, 2007, Conjunctive Bayesian Networks, Bernoulli 13(4), 893-909.

(56) References Cited

OTHER PUBLICATIONS

Berlin, 2014, Assembling large genomes with single-molecule sequencing and locality sensitive hashing, bioRxiv preprint (35 pages); retrieved from the internet on Jan. 29, 2015, at.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chang, 2005, The application of alternative splicing graphs in quantitative analysis of alternative splicing form from EST database, Int J Comp Appl Tech 22(1):14.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Compeau, 2011, How to apply de Bruijn graphs to genome assembly, Nat Biotech 29(11):987-991.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLoS Comput Biol 5(12): e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems, Bioinformatics 20(10):1546-1556.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hutchinson, 2014, Allele-specific methylation occurs at genetic variants associated with complex diseases, PLoS One 9(6):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/961156, filed Oct. 17, 2014 (19 pages).
International Search Report and Written Opinion dated Jan. 10, 2017, for International Patent Application No. PCT/US16/57324 with International Filing Date Oct. 17, 2016, (7 pages)
International Search Report and Written Opinion dated Mar. 19, 2015, for International Application No. PCT/US2014/061162 with International Filing Date Oct. 17, 2014, (12 pages).
International Search Report and Written Opinion dated May 11, 2015, for International Patent Application No. PCT/US2015/015375 with International Filing Date Feb. 11, 2015, (12 pages)
International Search Report and Written Opinion dated May 5, 2016, for International Patent Application No. PCT/US2016/020899, wiht International Filing Date Mar. 4, 2016, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).

(56) References Cited

OTHER PUBLICATIONS

International Search Report and Written Opinion dated Feb. 10, 2015, for International Patent Application No. PCT/US2014/060690, filed Oct. 15, 2014, PCT/US2014/060690 (11 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bonformatics 11(5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the Internet on Jun. 3, 2016, at.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Oshlack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.

(56) References Cited

OTHER PUBLICATIONS

Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5) 596-609.
Sosa, 2012, Next-Generation Sequencing of Human Mitochondrial Reference Genomes Uncovers High Heteroplasmy Frequency, PLoS One 8(10):e1002737.
Sturgeon, RCDA: a highly sensitive and specific alternatively spliced transcript assembly tool featuring upstream consecutive exon structures, Genomics, Dec. 2012, 100(6): 357-362.
Subramanian, 2006, DIALIGN-TX: greedy and progessive approaches for seament-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the Internet on Jun. 3, 2016, at.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pages 1-17, vol. 7:472; BMC Bioinformatics.
Wang, 2009, RNA-Seq: a revolutionary tool for transcriptomics, Nat Rev Genet 10(1):57-63.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.
Yu, 2010, The construction of a tetraploid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.

* cited by examiner

```
         ↓ 501

!"#$%&'()*+,-./0123456789:;<=>?@
000000000000010000000000000000000

ABCDEFGHIJKLMNOPQRSTUVWXYZ[\]^_`a
101000100000100001000000000000 bcdefghijklmnopqrstuvwxyz{|}~
00000000000000000000000000000
```

[0000]   [A, T, C, G]

[0001]   [A, T, C, G, -, N]

[0010]   [C, G]

[0011]   [A, T, C, G, -]

[0100]   [N]

[0101]   [-]

. . .

ADAPTION   BACKBAND   AGITATED

AIRPROOF   BALMIEST   ARCHIVAL

ASBESTOS   ADMITTER   ACCOUNTS

ACCOLADE   ACCURACY   ACCRUING

ACCURATE   ACCUSALS

 709

ABAABAAAAAAAAA, DAGIARSDCCCCCC,
ACIRLCBMCCCCC, PKTPMHEIOOURUU,
TBARIISTULRURS, IATOEVTTNAAIAA,
ONEOSAOETDCNTL, NDDFTLSRSEYGES

 113

ABAABAAAAAAAA  DAGIARSD
CCCCCCACIRLCBMCCCCCP  KTPMHEIOO
URUUTBARIISTULRURSIAT
OEVTTNAAIAAONEOSAOET  DCNTLNDDFTLSRS
EYGES (AB) (DAGIRS) (CAIRLBMP) (KTPMHEIO)
 1     3         3            3

(URTBAISL) (OEVTNAIS) (DCNTLFSR) (EYGS)
    3          3           3        2

[0000]  [OEVTNAIS]

[0001]  [URTBAISL]

[0010]  [KTPMHEIO]

[0011]  [CAIRLBMP]

[0100]  [DAGIRS]

```
┌─────────────────────────────────────┐
│ Determining a number of bits to     │
│ represent an integer                │
│                              1402   │
└─────────────────────────────────────┘
                  │
                  ▼
┌─────────────────────────────────────┐
│ Encoding the integer using the      │
│ determined number of bits           │
│                              1404   │
└─────────────────────────────────────┘
                  │
                  ▼
┌─────────────────────────────────────┐
│ Generating a header value that      │
│ indicates a total number of octets  │
│ representing the encoded integer    │
│                              1406   │
└─────────────────────────────────────┘
```

FIG. 14

| Number of Value Representation Length Bits | Number of Flags | Number of Value Representation Bits in Header Octet | Value Range | Code Size (Bytes) |
|---|---|---|---|---|
| 1 | 0 | 7 | $0..2^{15}-1$ | 1..2 |
| 1 | 1 | 6 | $0..2^{14}-1$ | 1..2 |
| 1 | 2 | 5 | $0..2^{13}-1$ | 1..2 |
| 1 | 3 | 4 | $0..2^{12}-1$ | 1..2 |
| 1 | 4 | 3 | $0..2^{11}-1$ | 1..2 |
| 1 | 5 | 2 | $0..2^{10}-1$ | 1..2 |
| 1 | 6 | 1 | $0..2^{9}-1$ | 1..2 |
| 1 | 7 | 0 | $0..2^{16}-1$ | 2..3 |
| 2 | 0 | 6 | $0..2^{30}-1$ | 1..4 |
| 2 | 1 | 5 | $0..2^{29}-1$ | 1..4 |
| 2 | 2 | 4 | $0..2^{28}-1$ | 1..4 |
| 2 | 3 | 3 | $0..2^{27}-1$ | 1..4 |
| 2 | 4 | 2 | $0..2^{26}-1$ | 1..4 |
| 2 | 5 | 1 | $0..2^{25}-1$ | 1..4 |
| 2 | 6 | 0 | $0..2^{32}-1$ | 2..5 |
| 3 | 0 | 5 | $0..2^{61}-1$ | 1..8 |
| 3 | 1 | 4 | $0..2^{60}-1$ | 1..8 |
| 3 | 2 | 3 | $0..2^{59}-1$ | 1..8 |
| 3 | 3 | 2 | $0..2^{58}-1$ | 1..8 |
| 3 | 4 | 1 | $0..2^{57}-1$ | 1..8 |
| 3 | 5 | 0 | $0..2^{64}-1$ | 2..9 |

FIG. 18

SYSTEMS AND METHODS FOR SEQUENCE ENCODING, STORAGE, AND COMPRESSION

SEQUENCE LISTING

This application contains a Sequence Listing which has been submitted electronically and is hereby incorporated by reference in its entirety. Said sequence listing, created on Nov. 14, 2017, is named SBG-027-23-ORG_Sequence_Listing.txt and is 3 KB in size. The content of which is identical to the written sequence listing and includes no new matter.

CROSS-REFERENCE TO RELATED APPLICATIONS

This application claims priority from U.S. Provisional Patent Application Ser. No. 62/338,706, filed on May 19, 2016, entitled "SYSTEMS AND METHODS FOR ENCODING GENOMIC INFORMATION", U.S. Provisional Patent Application Ser. No. 62/400,388, filed on Sep. 27, 2016, entitled "SYSTEMS AND METHODS FOR SEQUENCE ENCODING", U.S. Provisional Patent Application Ser. No. 62/400,411, filed on Sep. 27, 2016, entitled "SYSTEMS AND METHODS FOR METADATA STORAGE AND COMPRESSION", and U.S. Provisional Patent Application Ser. No. 62/400,123, filed on Sep. 27, 2016, entitled "SYSTEMS AND METHODS FOR GENOMIC GRAPH INSERT SPECIFICATION", the disclosures of which are hereby incorporated by reference.

TECHNICAL FIELD

The disclosure relates generally to systems and methods for use in medical genetics, genomic research, and next-generation sequence (NGS) analysis. In particular, this disclosure relates to systems and methods for encoding genomic information associated with sequence graphs.

BACKGROUND

Studying genomes can potentially reveal much about the health and history of organisms and entire species. Researchers can identify genes associated with cancer and other diseases through genomic studies, and genomics also plays an important role in forensics, genealogy, and agriculture, among other fields. A frequent approach to genomic studies includes sequencing DNA from a sample and comparing the resulting sequence reads to each other or to a known reference to characterize the genomes of organisms represented in the sample. Reference genomes often include whole genomes that have been sequenced and published, often available online. Variation among genomes has been represented by structuring genomic sequences as graphs.

Unfortunately, storing and analyzing genomic information has become impractical or impossible using conventional techniques. For example, as more genomes continue to be sequenced, the time required to store, query, and manage the new resulting information also increases. Many conventional compression techniques developed to transmit genomic information require custom or proprietary decoders, which further limits broad access. Representing genomes and genomic variations as graphs presents further complexities. Therefore, as the number of sequenced genomes and catalogued variations increases, analyzing and comparing the information quickly becomes intractable because of the required processing time or storage of such large data sets, especially when computational resources are limited.

Genetic information appears to be encoded using only four characters, A, C, G, and T, such that it could be written to a computer disk using only two bits per character. However, in real-world applications, genetic information generally requires more than 2 bits per character. For example, "-" typically represents a gap and "N" is used to represent an unknown nucleotide. Separate characters exist for bases such as inosine and uracil, and ambiguity characters are also sometimes employed. To include those characters, genetic sequences are often stored using an 8-bit per character format such as the UNICODE standard. This presents a problem in storing, analyzing, or transferring large genomic data sets.

Additionally, in order for genomic data to be used meaningfully, it must be stored with metadata. Metadata is notoriously difficult to deal with, as it tends to be diverse, unpredictable, and unwieldy. Metadata may include dates, text notes, patient IDs, and GenBank annotations, among other kinds of sample-related information. Indeed, the lack of predictability and structure in data is often what leads one to classify it as metadata in the first place. Among the many challenges in managing such data is compressing it. Compression often takes advantage of predictable patterns in data. Because metadata appears diverse and unpredictable, it appears particularly challenging to compress. Nevertheless, most genomic sequencing and analysis projects require metadata to be included with the sequence data. Due to the size of data sets resulting from next-generation sequencing (NGS) technologies, storing or transmitting large genomic data sets along with the required metadata can be impracticable.

SUMMARY

The present disclosure describes various systems and methods for encoding and compressing genomic information and, optionally, associated metadata. Variable-length encoding applies to a variety of formats of sequence data and genomic data, such as a multiple sequence alignment, a set of sequence read data, or a directed graph representing relationships among multiple genomic sequences. Since the variable length encoding may be applied to very large datasets, such as sequence reads, sequence alignments, sequence graphs (e.g., genomic graphs), very large genomic data sets may be encoded compactly. Since the variable length encoding embeds the number of bytes used (e.g., a length value) within the encoded information, a downstream decoder will not require prior knowledge of the number of bytes required for each component. Since the system can encode the data efficiently in terms of both compression ratio and time while also preserving the accuracy of the information, the size or required processing time are not limiting factors in analyses for medical genetics, genomic research, and next-generation sequencing (NGS).

In certain aspects, methods are provided for encoding genomic data. The method includes dividing genomic data into a plurality of segments and encoding characters within each of the plurality of segments with a smallest number of bits per character needed to represent all unique characters present in the respective segment. Within each segment, an identity and number of each character is correctly encoded and the data encoded is lossless—the original data can be recovered by a decoding operation. Constant-length encoding may be used wherein, within a segment, every character is encoded with the same number of bits. Encoding the characters within each of the plurality of segments may include determining a number N of unique characters in the segment and encoding the segment using X bits per character, where $2^{\wedge}(X-1)<N<2^{\wedge}X$. Encoding the characters within each of the plurality of segments may include creating for each segment a header and a corresponding data portion, wherein the header comprises information about an alphabet of characters that is encoded by the corresponding data portion. The header optionally includes at least two bits that indicate a length of the header and a plurality of flag bits that identify the alphabet of characters that is encoded by the corresponding data portion. In some embodiments, the flag bits identify the alphabet using a bitmap or mask to identify included characters.

Dividing the genomic data into the plurality of segments may be done dynamically, wherein segment boundaries are selected as to achieve maximum space savings. Dynamic boundary selection may be performed by scanning the genomic data and keeping track of a number of unique characters scanned; noting positions in the sequence where the number increases to a power of two; calculating a compression that would be obtained by dividing the genomic data into one of the plurality of segments at ones of the noted positions; and dividing the genomic data into the plurality of segments at the positions that yield the best compression.

For example, the system may isolate a homopolymer run or a series of dinucleotide repeats as a segment and encode that segment using one bit per character. A long stretch of DNA using only the canonical A, C, G, and T may be encoded using two bits per character, whereas portions of the genome that use an alphabet of more than four characters will be separately encoded with the appropriate number of bits per character. As the system scans along the genome, it may look ahead at possible segment boundaries and divide the genome into segments such that the alphabet size within each segment allows the genome to be encoded compactly. In this sense, the encoding is dynamic—the system chooses the boundaries as it progresses along the genomic data.

The dynamic alphabet encoding (DAC) is applicable to a variety of formats of sequence data and genomic data such as an organism's genome, a multiple sequence alignment, a set of sequence read data, or a directed graph representing relationships among multiple genomic sequences. In some embodiments, the genomic data that is encoded comprises a directed graph representing at least a portion of a plurality of genomes. Since DAC may be applied to very large data sets, such as sequence reads, sequence alignments, or genomic reference graphs, very large genomic data sets may be encoded very compactly. The method may be used in a process of serialization. Encoding the characters within each of the plurality of segments may transform the directed graph into a sequence of bits. The method may further include transferring the sequence of bits serially from a computer memory device of a computer system to a second computer system.

Since the encoding is dynamic, a system may begin encoding a large data set and begin streaming the encoded data as a series of bits without having yet read through every character of the entire data set. Since the system can encode dynamically without reading through the entire set, the size of such data sets are not a limiting factor in analyses for medical genetics, genomic research, and next-generation sequencing (NGS). Since the segments are chosen based on alphabet size, the system maximizes the potential advantage provided by the very nature of genomic data in that large stretches of (although not all of) genomes may be represented using two bits per character and that some stretches (e.g., homopolymer runs and dinucleotide repeats) may be represented using one bit per character of the alphabet. Thus disclosed systems and methods provide significant advances and advantages in technical fields of medical genetics, genomic research, and next-generation sequence (NGS) analysis.

Methods of the invention may achieve compression to final size smaller than 2 bits per character over the entire genomic data set. For example, where the genomic data consists of a number N of characters, all of the genomic data may be encoded into a final encoded data set of fewer than 2N bits. Preferably, the steps are performed using a processor of a computer system comprising a memory subsystem coupled to the processor, with the genomic data stored in the memory subsystem.

In certain aspects, a system is provided for encoding genomic data. The system includes a processor coupled to a tangible memory subsystem containing instructions. When the instructions are executed by the processor, the processor causes the system to divide genomic data into a plurality of segments and encode characters within each of the plurality of segments with a smallest number of bits per character needed to represent all unique characters present in the respective segment. Within a segment, every character is preferably encoded with the same number of bits (i.e., the system implements constant-length encoding within segments). To divide the genomic data into the plurality of segments dynamically, the system may: scan the genomic data and keep track of a number of unique characters scanned; note positions in the sequence where the number increases to a power of two; calculate a compression that would be obtained by dividing the genomic data into one of the plurality of segments at ones of the noted positions; and divide the genomic data into the plurality of segments at the positions that yield the best compression. To encode the characters within each of the plurality of segments, the system may determine a number N of unique characters in the segment (i.e., an alphabet size for that segment) and encode the segment using X bits per character, where $2^{\wedge}(x-1)<N<2^{\wedge}x$.

In some embodiments, encoding the characters within each of the plurality of segments includes using the processor for creating for each segment a header and a corresponding data portion, in which the header includes information about an alphabet of characters that is encoded by the corresponding data portion. The header may, for example, include at least two bits that indicate a length of the header and a plurality of flag bits that identify the alphabet of characters that is encoded by the corresponding data portion. In certain embodiments, the flag bits identify the alphabet using a bitmap to identify included characters.

In some embodiments, methods are provided for compressing metadata by organizing the metadata into a stream of bytes, re-ordering the bytes in a way that groups similar bytes, and then compressing local groups of similar bytes. The methods are applicable even where the metadata is not linear, such as metadata labels for a genomic graph. All of the bytes of metadata are placed into a linear order, creating a stream of bytes. The stream of bytes are re-ordered by a reversible operation that groups similar bytes within the re-ordered stream. Systems and methods then automatically break the re-ordered stream into segments that contain local pockets of self-similarity. Thus even where the original metadata uses a full alphabet of 256 characters, after the re-ordering and segmenting, some of the segments may include, for example, only 8 or 16 unique characters and can be encoded using only a few bits per byte. As a result, all of the metadata will be compressed by a significant amount. The segments are given headers that inform a subsequent de-coding operation.

Since the result is a linear stream of bits, the compressed metadata may be rapidly and easily transferred over communication networks, between computer systems, or into storage. Since the stream of bits can be de-coded into the bytes by reading the headers and then placed into the original order by a reverse of the reversible re-ordering operation, the original metadata can be recovered. Compression is essentially lossless, and can be performed automatically by a computer system that applies a set of rules. Since metadata can be automatically and losslessly compressed, it can be easily transferred or stored along with genomic data, allowing that genomic data to be used to its full potential in research and medical applications.

In certain aspects, methods are provided for compressing metadata. The methods include determining an order for a plurality of objects that each comprise a plurality of bytes, placing the bytes in a sequence within which the bytes are grouped by their position within the objects and wherein bytes within a group are in the determined order, dividing the sequence of bytes into a plurality of segments, and encoding bytes within each of the plurality of segments with a smallest number of bits per byte needed to represent all unique bytes present in each segment. At least a first segment and a second segment use a different number of bits per byte. Methods are preferably applicable to graph metadata wherein each object comprises metadata for a node or an edge of a graph such as a genome graph representing genetic sequences from a plurality of organisms. In certain embodiments, the genome graph has a graph geometry and graph content, and the genome graph and the metadata are stored in a memory subsystem within a computer system. The method may further include serializing the genome graph by serializing the graph geometry and the graph content into a stream of bytes, wherein the stream of bytes can be deserialized into a clone of the genome graph. The serializing may include serializing the graph geometry into a first stream of bytes, serializing the graph content into a second stream of bytes, and combining the first stream of bytes and the second stream of bytes into the stream of bytes.

Encoding the bytes within each of the plurality of segments may include creating for each segment a header and a corresponding data portion, in which the header comprises information about a set of included bytes that is encoded by the corresponding data portion. The header may include bits that indicate a length of the header and a plurality of flag bits, wherein the flag bits identify the set of included bytes that is encoded by the corresponding data portion. Preferably, within a segment, every byte is encoded with the same number of bits. Methods may include transferring the encoded bytes serially from a memory of a computer system to a second computer system.

In certain aspects, a system is provided for transferring data. The system includes a processor coupled to memory containing instructions that when executed by the processor cause the system to: determine an order for a plurality of objects that each comprise a plurality of bytes; place the bytes in a sequence within which the bytes are grouped by their position within the objects and wherein bytes within a group are in the determined order; divide the sequence of bytes into a plurality of segments; and encode bytes within each of the plurality of segments with a smallest number of bits per byte needed to represent all unique bytes present in each segment, wherein at least a first segment and a second segment use a different number of bits per byte. The system may be further operable to transfer the encoded bytes serially from the memory to a second computer system. Preferably, within a segment, the system encodes every byte with the same number of bits. In some embodiments, the system divides the sequence of bytes into the plurality of segments by: scanning the sequence of bytes and keeping track of a number of unique bytes scanned; noting positions in the sequence of bytes where the number increases to a power of two; calculating a compression that would be obtained by dividing the sequence of bytes into one of the plurality of segments at ones of the noted positions; and dividing the sequence of bytes into the plurality of segments at the positions that yield the best compression. The system may encode the bytes within each of the plurality of segments by creating for each segment a header and a corresponding data portion, in which the header comprises information about a set of included bytes that is encoded by the corresponding data portion. The header may include at least two bits that indicate a length of the header and a plurality of flag bits, wherein the flag bits identify the set of included bytes that is encoded by the corresponding data portion. The system may encode the bytes within each of the plurality of segments by determining a number N of unique bytes in the segment and encoding the segment using X bits per byte, where $2^{(x-1)}<N<2^x$.

In certain embodiments, each object comprises metadata for a node or an edge of a graph stored in the memory. The graph is a genome graph representing genetic sequences from a plurality of organisms. The genome graph includes a graph geometry and graph content. The system is operable to serialize the genome graph by serializing the graph geometry and the graph content into a stream of bytes, in which the stream of bytes can be deserialized into a clone of the genome graph.

These and other aspects, features, and implementations, and combinations of them may be expressed as apparatus, methods, means or steps for performing functions, components, systems, program products, and in other ways. Other aspects, features, and advantages will be apparent from the description and drawings, and from the claims.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9 shows reordering a stream of bytes and segmenting the reordered bytes.

FIG. 11 shows a cache of recently used alphabets according to certain embodiments including metadata compression.

FIG. 14 diagrams a method of encoding genomic data using a variable length encoding scheme.

FIG. 18 depicts a table showing how an encoding scheme according to the disclosure can be modified to accommodate both a variety of length bits and flags.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The methods and systems described throughout this disclosure provide an approach to encoding information (e.g., genetic information) that minimizes the number of required bytes, which is particularly advantageous when the information includes genomic or graph related data. As described throughout this disclosure, genetic information is written in a compact format by dynamically dividing the information into segments and encoding each segment with the smallest number of bits per character necessary for whatever alphabet of characters appears in that segment. The methods described herein are applicable to many types of data and information. In preferred embodiments, the methods are applied to bioinformatic data such as sequences, e.g., genomic sequences, and genomic sequences in graph references, and metadata.

Additionally, systems and methods described within may use empirical insights about metadata to provide an approach to compressing the metadata. Such insights include a tendency for metadata to show local or periodic similarity, repetition, or other patterns. Systems and methods described within place all of the bytes of metadata associated with a genomic data set into a linear order, creating a stream of bytes. The stream of bytes is re-ordered by a reversible operation that groups similar bytes within the re-ordered stream. Systems and methods then automatically break the re-ordered stream into segments in a way that limits a number of unique bytes in the segments, thereby creating local pockets of self-similarity.

Further, the detailed description set forth below in connection with the appended drawings is intended as a description of embodiments and does not represent the only forms which may be constructed and/or utilized. However, it is to be understood that the same or equivalent functions and sequences may be accomplished by different embodiments that are also intended to be encompassed within the spirit and scope of the disclosure.

Dynamic Alphabet Coding (DAC)

Figure 1:
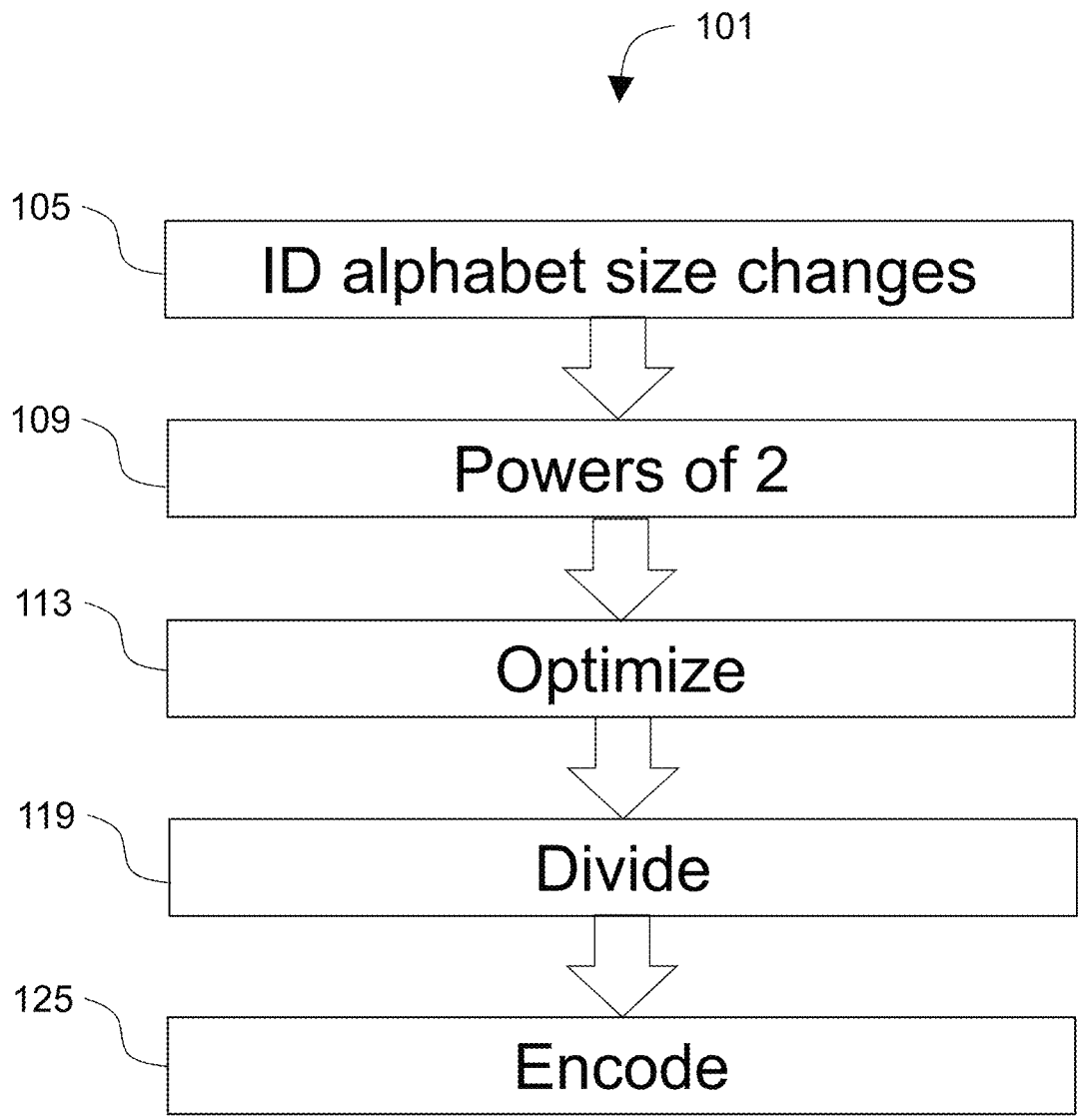
FIG. 1 diagrams a method of encoding data.

FIG. 1 diagrams a method 101 of encoding bioinformatic data. Using genomic sequence data as an example, a computer system scans along the genomic sequence data and dynamically chooses the segment boundaries that maximize space savings. The boundaries are chosen so that the resulting segments will have alphabet sizes conducive to compact encoding. The number of bits per character will be selected for each segment based on an alphabet size for that segment, which may be described as alphabet encoding. The encoding is dynamic in that the system chooses the boundaries as it progresses along the genomic data. In some embodiments, the system identifies 105 points along the sequence at which alphabet size will change and notes 109 those points at which the alphabet size will increase to a power of two (e.g., go from 3 to 4 or from 7 to 8). The system will choose from among those noted points that will optimize 113 compression and divide 119 the data at those points and encode 125 each segment. Thus, method 101 provides for DAC applicable to bioinformatic data.

The data will be divided 119 into segments. The number of unique symbols in each segment constitutes an individual alphabet. In some embodiments, segment data is encoded using constant length encoding, but the length of symbol representation differs for different segments. Symbol representation length is a function of the alphabet size. The smallest number of bits that is enough to represent all different unique symbols present in the segment is used.

For optimization 113, segment boundaries are selected to minimize the total representation size, which is the size of the data representation+size of additional information describing segment lengths and the alphabets. Note the additional information describing segment lengths and the alphabets. This additional information could be described as an "overhead" cost and limits the amount that the data can be divided 119 while still saving space. As an extreme example, if a genome were divided entirely into segments of length equal to 1 nucleotide, each nucleotide would require a header describing the length of that segment ("1 nt") and defining the included alphabet (i.e., the nucleotide). At this extreme, the encoding process would not be optimized for minimal size. Instead, the system chooses those segment boundaries that—given the requirement for certain "overhead" costs per segment—optimize for efficient compression.

For each segment, the alphabet of that segment is encoded. Different ways of encoding an alphabet for a segment may be used such as, for example, specifying the symbols of the alphabet; giving a bitmap over an inclusive alphabet; giving an index to a list of alphabets; or simply using some unrestricted alphabet. Thus, in some embodiments, the segment alphabet is encoded by explicitly specifying which symbols are included, which can be achieved either by using a bitmap (e.g., exists/does not exist) or by enumerating symbols one by one, whichever is more efficient. In certain embodiments, the segment alphabet can be encoded by having the system maintain a cache of recently used alphabets and indicating one of those alphabets that will be used for the current segment (e.g., by storing an index of one of the N most recent alphabets). In some situations, local data entropy is too high. The standard approach of using a limited alphabet can be ineffective. In such cases, the unrestricted alphabet (i.e., all possible symbols AKA "copy" mode) is used. For those specific situations, a special indicator is reserved (e.g., a special combination of bits, etc.). The system selects one of the three approaches (explicitly specify symbols; index entry in a cache; and use unrestricted alphabet) based on which of these gives the best result in terms of combined (alphabet+ data) representation size. A unique code combination may be used to indicate which of those approaches is selected and how it is applied.

Systems and methods of the invention implement the technique just described broadly. In preferred embodiments, the DAC technique is implemented for bioinformatic data. Bioinformatic data may be particularly well-suited to the DAC technique because such data: (i) is often generated over small alphabets; (ii) often contains many repetitive sequences; and (iii) is often very large (e.g., at gigabyte, terabyte, or petabyte scale). The DAC techniques described herein exploit those features to create a compression method that, though applicable to any kind of data, is particularly effective in compressing bioinformatic data.

Compression can be made more efficient by taking account of the frequencies with which different characters appear. (Huffman codes are one canonical application of this idea.) By making frequent data less space-intensive, less space is used. Most algorithms exploiting this fact, however, judge the frequency of a given symbol globally, not locally. That is, the criteria by which it is judged how frequent a symbol is are insensitive to the fact that there can be considerable local variation in the frequencies of symbols. In the case of bioinformatic data this leads to unpalatable consequences. One extreme example of this is the human genome as represented in HG19; chromosome 1 begins with fifty thousand N's, representing an unknown region at the 5' end of the sequence. While it might be reasonable to assume that A's account for between 22% and 26% of chromosome 1, it is highly inaccurate to suppose that a given character near the beginning of chromosome 1 is an A with that likelihood.

As an extreme example of DAC, systems and methods of the invention may divide the first 50,000 characters of chromosome 1 of hg19 into a first segment, with the remainder into other segments. That first segment may then be encoded with a header and a representation of the data. The header will show, among other things, that the alphabet used in the representation of the data consists of 1 character, that the character is "N", and that each nucleotide of the segment will be encoded using one bit.

More generally, systems and methods of the invention encode text that includes considerable local variation in the frequencies of symbols in a way that compresses the data. Systems and methods described herein divide a given text into sections and compress each section individually, with respect to its own alphabet. The system automatically optimizes compression in view of the overhead required for each section. The overhead represents the additional information that must be encoded for the system to be able to decode the individual sections. In particular, overhead can include: section location, section length, section alphabet. This will affect representation efficiency. With the increase of the number of sections, the amount of the additional information increases. On the other hand, sections become smaller, which results in smaller alphabets, which, in turn, results in a more efficient data encoding within each individual section. In the context of bioinformatics and in other contexts also, the savings of using "local alphabets" overwhelms the cost of that overhead. Moreover, other benefits are achieved.

Systems and methods described herein divide the overall algorithm into a few sub-processes, each of which again could be treated as a "black box" and optimized separately.

An important step of methods of the invention is to divide 119 the text into "local" chunks. Dividing 119 the text may be accomplished in any number of ways. For example, any number of algorithms composed in the "greedy" paradigm could be imagined. A greedy algorithm would make sequential scans through the data, looking for the part of the sequence most amenable to compression with an alphabet of which the size is a power of 2. That part would be encoded, and the process would be repeated on the rest.

In a preferred embodiment, the sequence is scanned and a number of letters required to give the full sequence up to that point is tracked.

Figure 2:
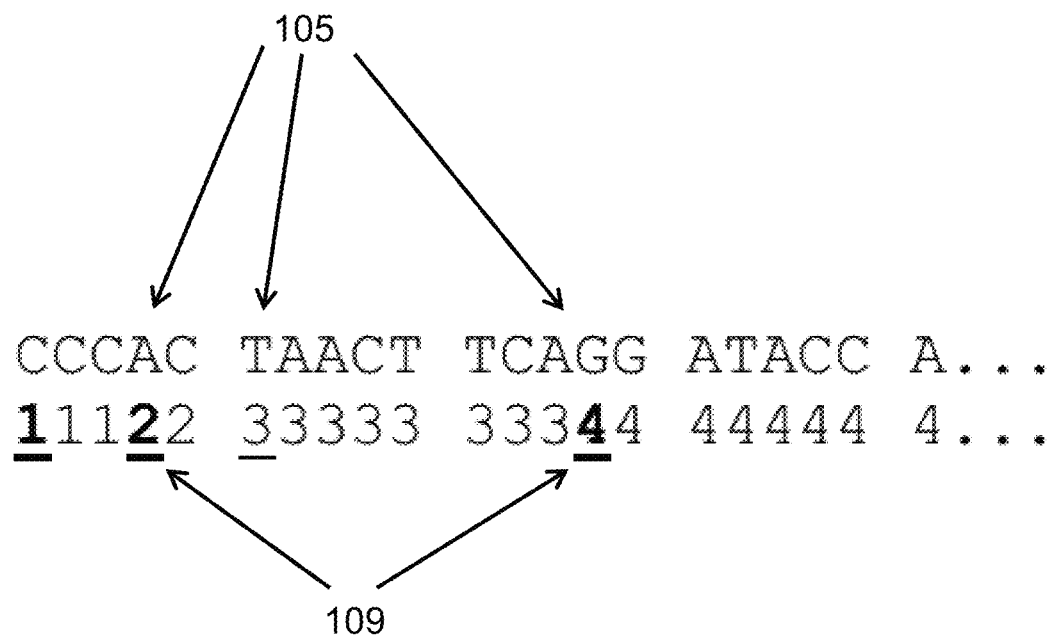
FIG. 2 shows candidate breakpoints in a sequence.

FIG. 2 shows the sequence CCCAC TAACT TCAGG ATACC A (SEQ ID NO. 1). As the system scans along the sequence, the system identifies 105 points along the sequence at which alphabet size will change and notes 109 those points at which the alphabet size will increase to a power of two (e.g., go from 3 to 4 or from 7 to 8). The string of numbers in FIG. 2 gives—for each position—the number of characters required to represent the sequence up to that position. The underlined positions indicate where the number increases. These numbers that are boldface denote 109 the powers of two. The powers of two are the relevant break-points for the preferred embodiments, because the fact that constant-length encoding will be used in the next stage means that all numbers of characters between $2^N+1$ and $2^{(N+1)}$ will require the same number of bits per character to encode.

Whenever one of these relevant break-points is encountered, the system calculates how much space it would take to encode the sequence with an alphabet of that size. (Both the size of the header and the size of the constant-length data portion are taken into account in this calculation.) The efficiency of the representation is then calculated, and these efficiency figures can be compared in order to determine the best alphabet size for a given region, thereby choosing the break-points that optimize 113 the compression. Thus it can be seen that systems and methods disclosed herein are useful to divide 119 the genomic data into the plurality of segments by: scanning the genomic data and keeping track 105 of a number of unique characters scanned; noting 109 positions in the sequence where the number increases to a power of two; calculating a compression that would be obtained by dividing the genomic data into one of the plurality of segments at ones of the noted positions; and dividing 119 the genomic data into the plurality of segments at the positions that yield the optimized 113 compression.

Any suitable method can be used to choose the breaks that optimize 113 the compression. One reasonable rule to apply at this stage is that if a given alphabet size is more efficient than the next two larger alphabet sizes, that alphabet should be used, and the process should be re-started after that section. So, for example, if the efficiency calculated at the location corresponding to 2 is better than that at the locations corresponding to 4 and 8, it is to be used, and the process begins again at the next location. With the optimal break-points selected, the system then divides 119 the text into segments and encodes 125 each segment.

Figure 3:
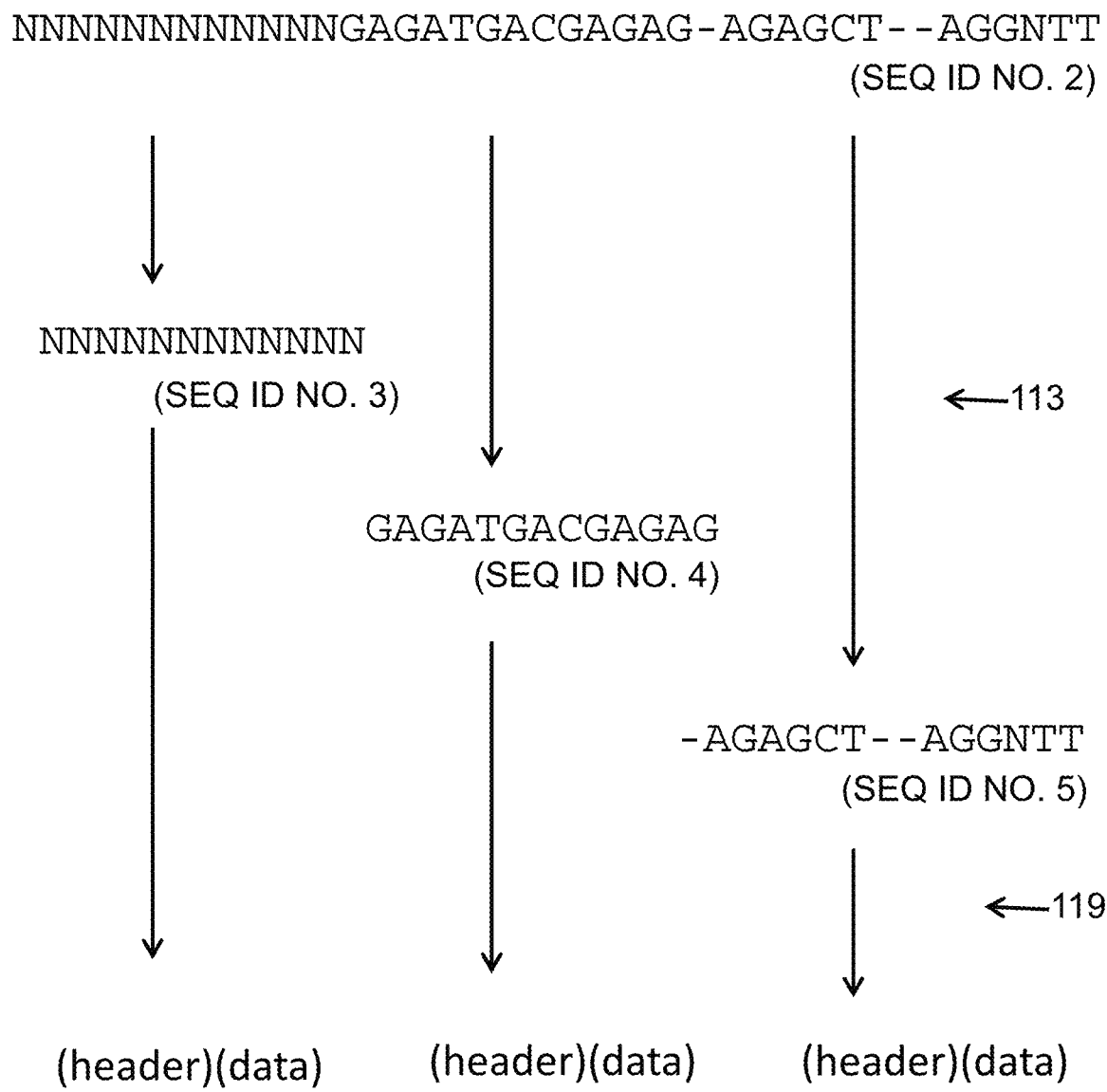
FIG. 3 shows how genomic data may be divided into segments and encoded.

FIG. 3 shows how genomic data may be divided 113 into a plurality of segments and how characters within each of those segments may be encoded 119. To illustrate the method, FIG. 3 shows NNNNNNNNNNNNGAGATGAC-GAGAG-AGAGCT-AGGNTT (SEQ ID NO. 2). The given example is chosen to illustrate different alphabet sizes that may be invoked with a particular division. As shown in FIG. 3, the original genomic data is divided 113 into three segments. The first segment includes NNNNNNNNNNNN (SEQ ID NO. 3). The second segment includes GAGAT-GACGAGAG (SEQ ID NO. 4). The third segment includes -AGAGCT-AGGNTT (SEQ ID NO.5). It should be discernable by visual inspection that the alphabet for the first section is a single character ("N"). The alphabet for the second section is four characters, and thus the second section could be encoded using 2 bits per character. The alphabet of the third section requires six characters (A, C, G, T, -, and N) and thus requires at least 3 bits per character. Once the data is divided 113, it is encoded 119.

Once the genomic data is divided into a plurality of segments, it can be efficiently and compactly encoded according to the following encoding scheme. In a preferred embodiment, each section is divided into two parts: a header, and a data representation. The header provides information about the encoded text, such as the alphabet used and the length (i.e., number of symbols) of the section, allowing for the data representation to be interpreted accurately. The data representation can be decoded based on the alphabet and a function from binary strings to elements of that alphabet. In certain embodiments, the compactness achieved is so great that only constant-length encoding of the data representation is required.

The header can be interpreted to decode the data. A computer system may be programmed with instructions that when executed by a processor cause the system to interpret the header and use that information to decode the data. In certain embodiments, the header is encoded according to a scheme that depicts a length of what is encoded, certain useful flags, and the encoded representation, all using 8-bit octets (where the encoded representation here will be a length of the data section, such as the number of octets following the header octet). Thus methods and systems of the invention implement a length-flags-representation (LFR8) 8 bit scheme.

Figure 4A:
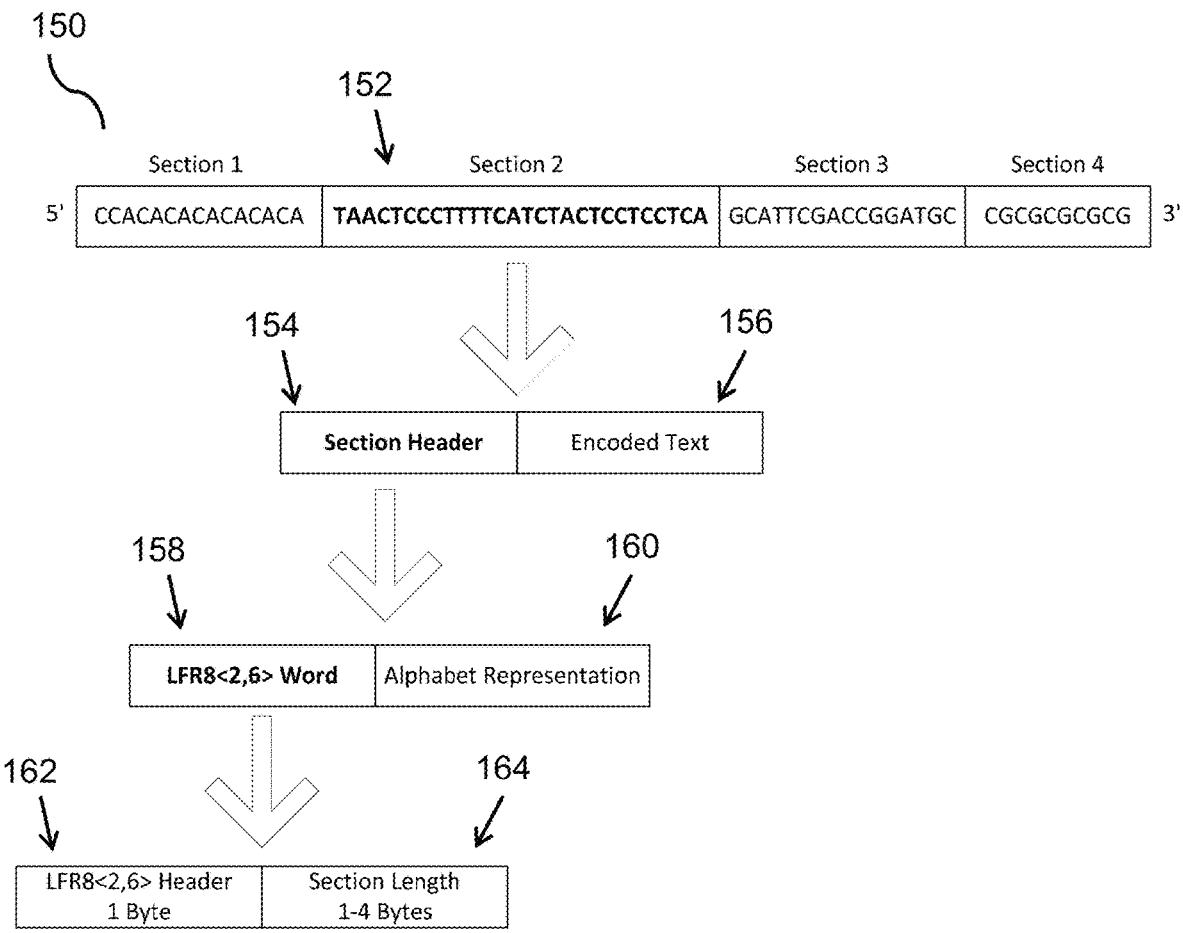
FIGS. 4A-B are diagrams illustrating the structure of encoded segments of nucleotide data as stored in computer memory.
Figure 4B:
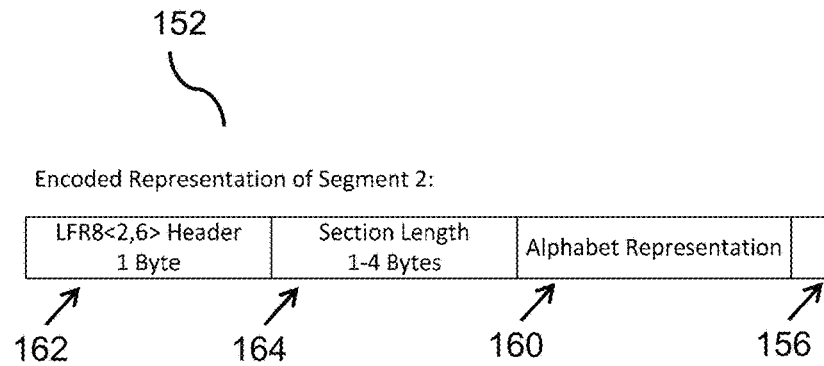

FIGS. 4A-B depict an example embodiment of encoded sequence data 150. As shown, the encoded sequence data 150 comprises four sections. FIG. 4A illustrates how the second section 152 may be encoded. As shown in FIG. 4A, the encoded representation of the second section 152 comprises a section header 154 and a data representation, such as encoded text 156. The section header further comprises an LFR8<2,6> word 158 and an alphabet representation 160. The LFR8<2,6> word 158 further comprises a LFR8<2,6> header 162 (1 byte) and a section length 164 (1-4 bytes). The section length 164 indicates the length of the encoded text 156, and the alphabet representation 160 indicates the alphabet used by the encoded text 156.

FIG. 4B illustrates the entire encoded representation of section 2, including the LFR8<2,6> header 162, section length 164, alphabet representation 160, and encoded text 156. The LFR8<2,6> word 158 follows the LFR8/LR8 format, which is described in more detail below. Briefly, LFR8 is a versatile encoding format that allows for the representation of integers along with useful information, such as flags. An LFR8<2,6> word describes a data structure having at least one header octet, in which the first two bits of the header octet indicate a number of octets following the header octet (which encode an integer, such as the section length 164), and the remaining six bits are reserved as flags. As only two bits are provided to indicate the section length (00, 01, 10, 11), then the LFR8<2,6> format can indicate that the section length is encoded using 1, 2, 3, or 4 bytes. Systems and methods of the disclosure may implement a modified LFR8 data structure in which the LFR8 encoded integer specifies a length of an encoded section following the LFR8 encoded integer, and further the flag bits of the LFR8 integer specify an alphabet to be used.

In LFR8<2,6> format, following the two ("2") length bits are six ("6") flag bits. The flag bits may be used to identify the alphabet used by the corresponding encoded text 156. The alphabet used may be identified in a variety of ways. For example, the flags may indicate that the alphabet is the full alphabet (e.g., the ASCII or UNICODE alphabet), in which case the text is encoded using, e.g., 8-bit octets in which each octet represents a symbol in the alphabet. The flags may also indicate that the alphabet can be determined using a mask over the full alphabet, which mask may be supplied as the alphabet representation within the encoded representation. The flags may also indicate that the alphabet itself is stored within the encoded representation, e.g. as a sequence of octets, wherein each octet indicates a character in the alphabet used by the encoded representation. As shown in FIG. 4B, the sequence of octets may be stored with the encoded representation as the alphabet representation. Additionally, the flags may also indicate that the alphabet used by the representation is stored in a "last recently used" (LRU) alphabet list or data structure, which may be stored separately from the encoded representation. This may be referred to as "LRU" mode.

In this embodiment, if the first flag bit is 0, the alphabet used by the encoded representation may be determined using a ternary decision procedure, which depends on the last five flag bits. First, if those five bits are "11111", the alphabet is assumed to be in "copy mode", i.e. using the unrestricted "full alphabet" (e.g., an alphabet containing 256 symbols). It is noted that the majority of modern computers rely on byte (8-bit) representation. So 256 symbols is the maximum alphabet size if each symbol is stored in a separate byte. However, if necessary the maximum alphabet size can be extended. The main idea of including this special bit combination is to emphasize the importance of the special case, when we use the entire (unrestricted) alphabet. Preferably, copy mode may be used where segmenting the data would not optimize the representation. As a hypothetical example, one may want to encode the following string (written over two lines merely due to its length):

! "#$%& ' ( ) * + , - . / 0123456789 : ; <=>?@ABCDEFGHIJKLMNO
PQRSTUVWXYZ [ \ ] ^_ ` abcdefghijklmnopqrstuvwxyz { | } ~

In such a case, no division would optimize the representation. Thus the full alphabet will be used and the last five bits of the 6 bit flag will be 11111. In this case, each octet of the encoded text would encode for one symbol of the associated sequence or string.

Figure 5:
FIG. 5 shows a bitmap mask that identifies an alphabet.

If, instead, those five bits are "11110", the alphabet is assumed to be in "mask mode", and the alphabet representation may represent the alphabet by being interpretable as a "mask" on the full 256-character alphabet. FIG. 5 shows an exemplary mask 501 that identifies the alphabet using a bitmap to identify included characters. In the depicted example, the alphabet would not be included. The alphabet is drawn on FIG. 5 to illustrate the way in which the bits operate as mask indicating characters of the alphabet. In the depicted embodiment, after the flag bits, the alphabet representation contains 256 bits, with the $n^{th}$ bit representing the $n^{th}$ of the 256 characters; a 1 indicates that the character is included in the alphabet, whereas a 0 indicates that it is not present in the alphabet. Thus, in this depicted example, after the flag bits the alphabet representation includes:

| | | | | | |
|---|---|---|---|---|---|
| 00000000 | 00000100 | 00000000 | 00000000 | 01010001 | 00000010 |
| 00001000 | 00000000 | 00000000 | 00000000 | 00000000 | 00000000 |

(with spaces included merely to aid reproduction and visualization).

As another example, in the event that the last five bits of the flag are 11110 and the rest of the alphabet representation includes:

| | | | | | |
|---|---|---|---|---|---|
| 00000000 | 00000100 | 00000000 | 00000000 | 01010001 | 00000010 |
| 00001000 | 00000000 | 00000000 | 00000000 | 00000000 | 00000000 | then the alphabet is {-, A, C, G, N, T}.

In some cases, the last five bits of the flag bits will not be 11111 or 11110. If those five bits are something other than 11111 or 11110, they are interpreted as a number representing the size of the alphabet. The alphabet representation is then to be interpreted as a sequence of that many 8-bit elements, each element representing an eight-bit constant-length encoding of a position in the full 256-character alphabet corresponding to a character of the alphabet. So, for example, if those five bits are 00011, we will expect the next 24 bits to be interpretable as three eight-bit sequences indicating positions in the 256-character full alphabet. Or better phrased, "representing indexes of specific characters in 256-character alphabet".

Consider the following 24 bits:
00010010 01000101 10101111
(Again, the spaces are only intended to make the string more readable.) For those bits, the system can determine that the alphabet consists of the $00100010^{th}$, 01000101th, and $1010111^{th}$ elements of the 256-character full alphabet (that is, the $34^{th}$, $69^{th}$, and $175^{th}$ elements, once translated from binary to decimal).

Thus, after the LFR8<2,6> word 158, the alphabet representation 160 (if needed) can be either a bitmap mask or a sequence of that many 8-bit elements, each element representing an eight-bit constant-length encoding of a position in the full 256-character alphabet corresponding to a character of the alphabet. That ends the section header 154. What follows the section header 154 of a segment is the data (i.e., the encoded text 156) of that segment. Systems and methods of the disclosure use information from the header as a guide to interpreting the data representation.

Figure 6:
FIG. 6 shows a cache of recently used alphabets.

In some cases, the flag bits may indicate that the alphabet can be determined by consulting a "Last Recently Used" (LRU) list. FIG. 6 shows a historical LRU-list 601 of alphabets according to certain embodiments. The LRU-list 601 may be a dynamic list of the sixteen most recently used alphabets, for example. In this embodiment, if the first flag of the flags in the LFR8<2,6> header is 1 (indicating that the alphabet is on this list) the last four of the six flag bits indicate the position on the list of the alphabet. This may be done in the obvious sequential way, so that 0000 is the first position, 0001 the second, 0010 the third, and so on to 1111 (the sixteenth position).

Note that the number of entries in the dynamic list is an adjustable parameter of the method. A list of eight alphabets, for example, could also be used. If the LRU-list 601 included eight alphabets, the last three bits would be used to represent the position in that list. Other details of the method and flags could be changed to accommodate lists of other sizes. That said, it may be found that a list of 16 alphabets gives good efficiency for genomic data. Note also that although one in principle could use a static list of 16 (or however many) alphabets, much can be gained by making the list dynamic. This exploits data locality—that is, the tendency of nearby data to resemble each other. A dynamic list thus keeps alphabets that have recently been useful on the list, and those alphabets are disproportionately likely to be useful.

The efficiency of the DAC approach is so great that constant-length encoding in the data representation section of each block can suffice for an efficient representation of that section. Moreover, it is in general unlikely for variable-length encodings to be useful in the sections that will arise in this DAC process, as these sections are chosen precisely to avoid situations in which less-frequent characters "clutter up" a section of data.

Therefore, each character of the section can be represented in log 2(i) bits, where i is the size of the alphabet for the section. (This logarithm is to be rounded up to the next integer if it is not an integer.)

Note that the techniques suggest a constant-length encoding scheme at this stage; because this relatively simple technique is used at this stage, it is only necessary to know (i) the sub-alphabet and (ii) the length of the section in order to know how to decode the upcoming section. That is, using a constant-length scheme at this stage makes it possible to put far less information in the headers. If variable-length techniques were used at this stage, that information would not suffice for the header, as one would also need to know something about the variable-length scheme (or at least the relative frequencies of the characters in the alphabet) in order to know how to decode the section.

A mapping from characters to constant-length codes may be explicitly provided but preferably an implicit mapping is used. Since the up-to-256 characters are given an order that does not change throughout the whole process, the characters in any sub-alphabet are also implicitly "in order" and this order can be assumed to correspond to the numerical order of the constant-length codes. For sub-alphabets of length 4, for example, 00 can be assumed to correspond to the symbol with the lowest index, 01 to the symbol with the next-lowest index, 10 to the symbol with the third-lowest index, and 11 to the symbol with the highest index.)

In a specific example, if the sub alphabet is (A, C, G, T), then 00 is A, 01 is C, 10 is G, and 11 is T.

It may be preferable to pad the section to keep its total length a multiple of 8 bits. (This makes the file easier to manipulate.)

Application of DAC to Metadata

Systems and methods described within are applicable to metadata that is associated with a non-linear structure. For example, graph data structures used in genomics and medical genetics often include sequence data and metadata. To the extent that units of metadata are associated with elements of the graph data structure, the metadata itself is structured according to the graph. The graph metadata is transformed into a linear structure, re-ordered, segmented, and encoded based on an alphabet from which the metadata is within each segment. After the linearization and before the encoding, a transformation is preferably applied to the linear metadata to re-order the bits to create the local regions of increased self-similarity (aka local regions of restricted alphabet size). The transformation makes the metadata an ideal candidate for a dynamic alphabet encoding (DAC) technique. The encoding is done dynamically, as a system proceeds through the linearized data and identifies breakpoints at which to break the metadata into segments that exhibit internal self-similarity enough that the alphabet of a segment can be recoded with fewer bits per byte, thereby compressing the data. The described operations are readily intelligible, easily implemented, and fast.

In an illustrative example, metadata is associated with the edges of a directed graph, and each metadata unit is 8 bytes long. Those bytes may directly represent the metadata; alternatively, a byte may function as a pointer to a memory location in which the metadata is stored. The record size of the metadata is a parameter of this method; 8 bytes is a value for this parameter that will be suitable for many applications.

The aforementioned insight is that metadata tends to show local or periodic patterns such as similarity, repeats, or serial changes. That is, whatever is true of a graph element such that a given piece of metadata applies to it is often also true of adjacent or periodically distributed graph elements. In bioinformatic contexts, such factors may pertain to the origin of a nucleic acid sample, the species with which a sequence is associated, the year in which a variant was added to a graph, the disease with which a sequence is associated, etc.

If there are many pieces of identical or near-identical metadata, however, that also means that there will be regions of the graph in which the metadata can be expressed with subsets of an alphabet. Even if these regions are not easily predicted in advance, DAC effectively compresses objects which contain such regions.

Figure 7:
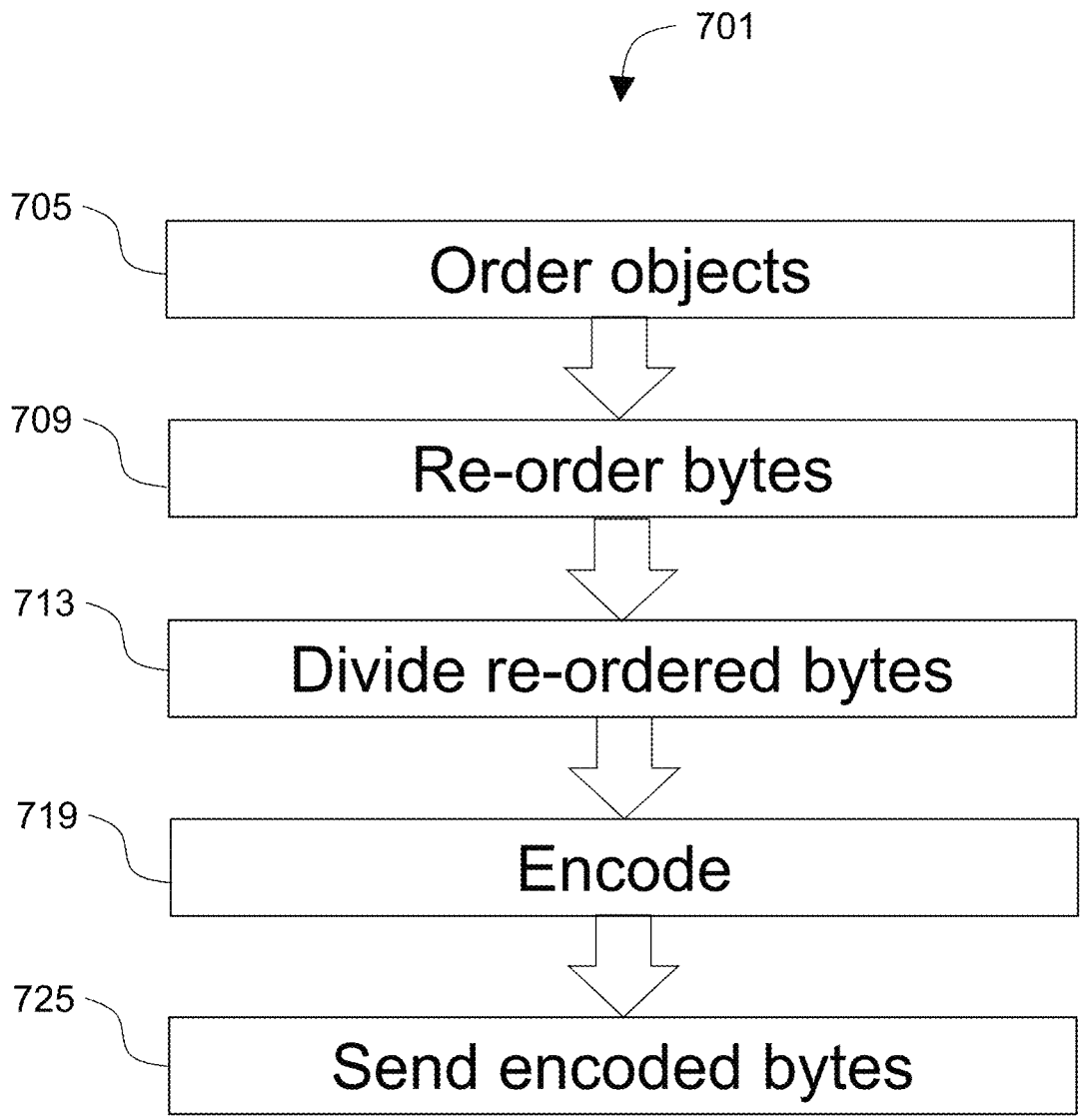
FIG. 7 diagrams a method of encoding and transmitting compressed metadata.

FIG. 7 diagrams a method 701 of compressing data (e.g., metadata). The method 701 includes determining 705 an order for a plurality of objects that each comprise a plurality of bytes and then reordering 709 the bytes. Any reversible reordering may be used to cluster similar elements. For example, a Burroughs-Wheeler transform may be performed. In a preferred embodiment, reordering 709 the bytes includes placing the bytes in a sequence within which the bytes are grouped by their position within the objects and wherein bytes within a group are in the determined order. The sequence of re-ordered bytes is then divided 713 into a plurality of segments. Within each of the plurality of segments, the bytes are encoded 719 with a smallest number of bits per byte needed to represent all unique bytes present in each segment, wherein at least a first segment and a second segment use a different number of bits per byte. The encoded bytes are then sent 725 to another computer system or to storage.

The method operates by re-ordering, segmenting, and encoding a sequence of bytes. Thus where the original metadata is not in a linear order a step of the method 701 may include placing 705 the metadata in a linear order. For example, where the metadata is associated with a genome graph, an initial step may be to traverse the graph and put 705 the metadata from each node into an order. The idea of this pre-processing step is "linearization." Where metadata is originally stored in a graph, the objective is to convert the metadata into a sequential representation. The rest of the method 701 operates on metadata that is in some linear order. Because the metadata is metadata of a graph, it comes in a structure that is not linear, and it is here linearized. Graph metadata may be linearized by any operation that roughly preserves proximity of edges (or nodes). That is, any method by which edges that are close on the graph are close in the traversal (at least often enough) will suffice. Even elementary approaches such as breadth-first search will produce more than acceptable results.

Methods of the invention may include an optional step that improves compression. Optionally, the bytes are replaced with the differences of the bytes and the previous bytes, according to the orientation rule applicable to the data type at hand. For a genome graph, the orientation rule may be to proceed in a 5' to 3' direction (or vice versa). Thus in some embodiments, systems and methods use metadata from one of the edges (specific edge is selected using some rule) incoming into the vertex for which the current edge is outgoing. Although it is helpful to ensure that the metadata for this "reference" edge has been already processed; otherwise 0 is used. (By "5' end" we mean data from the graph element immediately preceding the current graph element on a path. In bioinformatics applications, this corresponds to the 5' end of a nucleic acid. If the metadata for this preceding element has not been processed, or if there is no preceding element, zero is used for this value, so that the calculated difference equals the metadata value itself.) Specifically, replace the first of the eight bytes with the difference between that first byte and the first byte of the metadata of the graph element at the 5' end of that element; replace the second of the eight bytes with the difference between that second byte and the second byte of the metadata at the 5' end; and so on. This optional step is intended to be used in cases when the metadata increments steadily as the graph proceeds (perhaps because the metadata has something to do with distance from one end of the graph, the time at which a graph element was appended to the graph, or something else; just as it is an empirical fact that much metadata is constant among nearby graph elements, it is also true that metadata sometimes steadily increments or decrements in nearby graph elements). When this is the case, using this option will tend to produce many identical bytes of metadata among nearby graph elements, because the constant differences that one sees in cases of steady incrementing will be transformed into constants.

After determining 705 an order for the objects (which implicitly places all of the bytes into a sequence), the sequence of bytes is reordered 709 into a sequence within which the bytes are grouped by their position within the objects and wherein bytes within a group are in the determined order. In some embodiments, the bytes are reshuffled according to an operation that could be described as an interleaving or a transposition.

Figure 8:
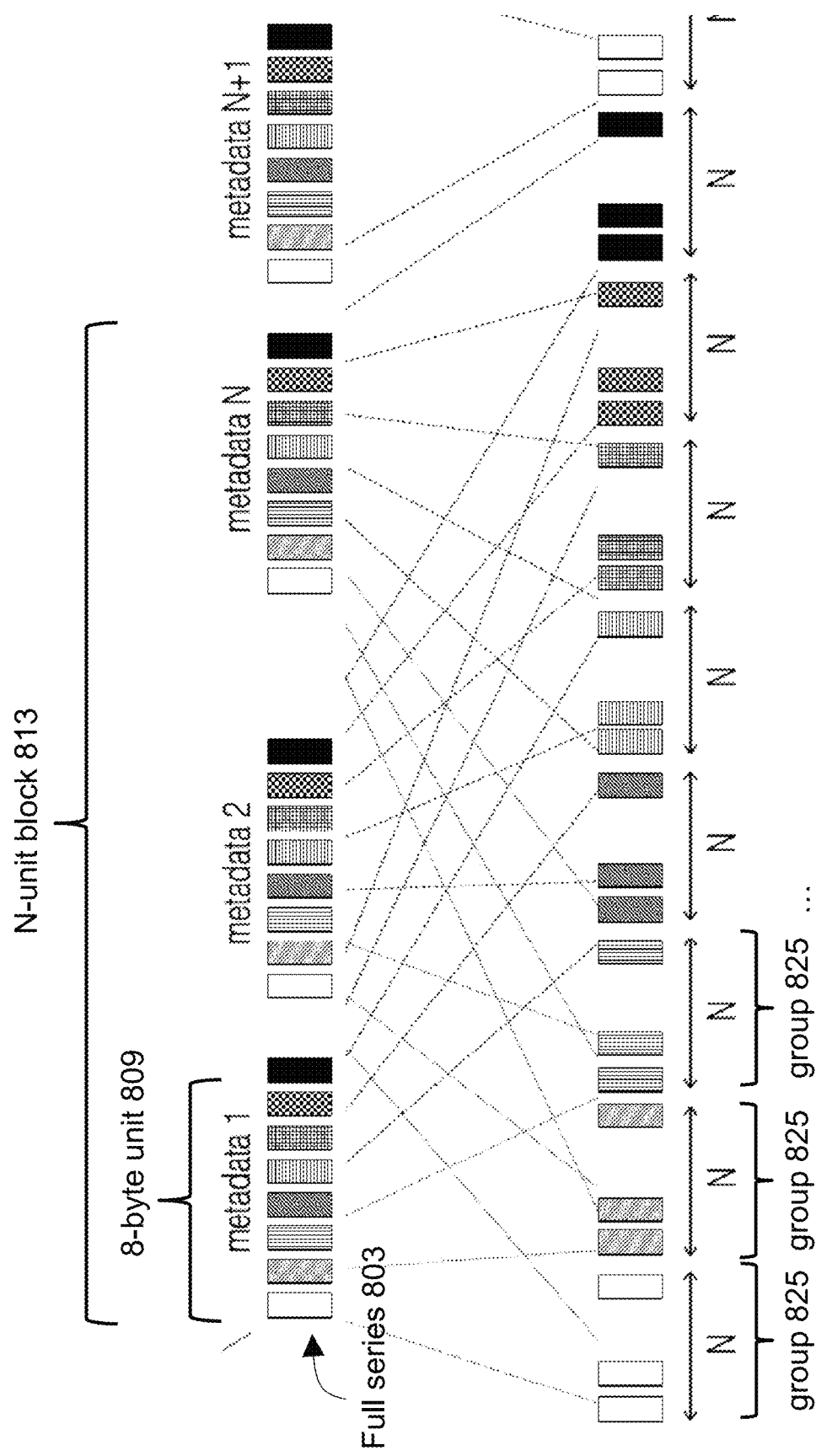
FIG. 8 diagrams an interleaving operation in which bytes are reordered.

FIG. 8 diagrams an interleaving operation in which bytes are re-ordered 709. Any suitable re-ordering of bytes may be performed that is reversible and that tends to create local areas of increased self-similarity. As shown, each block of metadata can comprise an 8-byte unit 809. In the depicted embodiment, the bytes of the series of objects are interleaved as follows: First, the full series 803 of 8-byte metadata units 809 are divided into N-unit blocks 813 of N consecutive 8-byte units 809 (where N is a parameter of the algorithm; a default setting may be $2^{15}$ in some embodiments). Each byte may be given an index indicating which 8-byte unit 209 that byte originates within, where the index is an integer between 1 and N, inclusive.

Then, for each N-unit block 813, the first bytes of all of the 8-byte units 809 of that block are grouped within a group 825 in order by index, after which the second bytes of all of the unites of that block are placed in order within a second group 825. This is continued through the eighth bytes. Those rearranged sets of bytes are concatenated into a sequence.

By those steps, the plurality of bytes of the full series 803 have been re-ordered 709 into a sequence within which the bytes are grouped by their position within the 8-byte units 809 and wherein bytes within a group 825 are in an ordered determined by their relative order within the original full series 803.

It will be appreciated that this operation has properties in common with a transpose. For N objects of metadata in which each object comprises M bytes, each object can be taken as a row of an N×M matrix B. The first column of B will include the first byte from each object. The second column of B will include the second byte from each object, and so on. If the matrix B is transposed into $B^T$, and then a stream of bytes is made by taking each row of $B^T$ in order starting with the first, then the resulting stream of bytes will be the same interleaved bytes as described in FIG. 8.

Once the bytes are re-ordered 709, the sequence of re-ordered bytes is then divided 713 into a plurality of segments. Dividing 713 into segments and encoding 719 is preferably done via a DAC operation described herein. Note that the re-ordering 709 will tend to leave similar/identical bytes together, so there should be local regions describable with small alphabets. Note that everything in method 701 is easily reversible.

The re-ordered stream of bytes may then be written in a compact format by DAC, which includes dividing the stream into segments and encoding each segment with the smallest number of bits per byte necessary for an "alphabet" of unique bytes that appears in that segment.

FIG. 9 diagrams an example of reordering 709 a stream of bytes and dividing the bytes into segments to optimize 113 representation size. In the illustrated example, the metadata contains 8-byte objects (here, the words "adaption", "backband", "agitated", etc.). Thus the initial stream of bytes begins, "adapationbackbandagitated . . . " The bytes are reordered 709 by the interleaving option and the re-ordered string begins "ABAABAAAAAAAAADAGIARSDC-CCCCCACIRLCB . . . " (in the middle of FIG. 9, commas and spaces are included to aid visualization). A computer system then divides the re-ordered bytes into segments at boundaries that allow for compact encoding. For example, if the first segment is ABAABA AAAAAAAA, then that first segment can be recoded using 1 bit per byte. The encoding may provide that A=1 and B=0. In this case, the segment would be re-coded as 10110111111111. The next segment is DAGIARSD and the alphabet for that next segment is DAGIRS. This is then encoded 125 using three bits per byte.

For each segment, the alphabet of that segment is encoded.

It is worth noting that the unique atoms of data under consideration are bytes. A byte is a set of 8 bits. A bit can have two values. Thus, a byte may have up to $2^8$ values, which is 256 values. Many computer environments use a standard such as UNICODE to map bytes to familiar keyboard characters objectively. Thus, in many contexts, byte and character will be interchangeable. In such contexts, it will be appreciated that it is very natural to refer to an alphabet of bytes. Within the context of alphabet encoding and the following discussion, character and byte are used substantially interchangeably.

An important step of the methods described within is to divide 119 the text into "local" chunks. Dividing 119 the text may be accomplished in any number of ways. For example, any number of algorithms composed in the "greedy" paradigm could be imagined. A greedy algorithm would make sequential scans through the data, looking for the part of the sequence most amenable to compression with an alphabet of which the size is a power of 2. That part would be encoded, and the process would be repeated on the rest.

In a preferred embodiment, the sequence is scanned and a number of letters required to give the full sequence up to that point is tracked.

Figure 10:
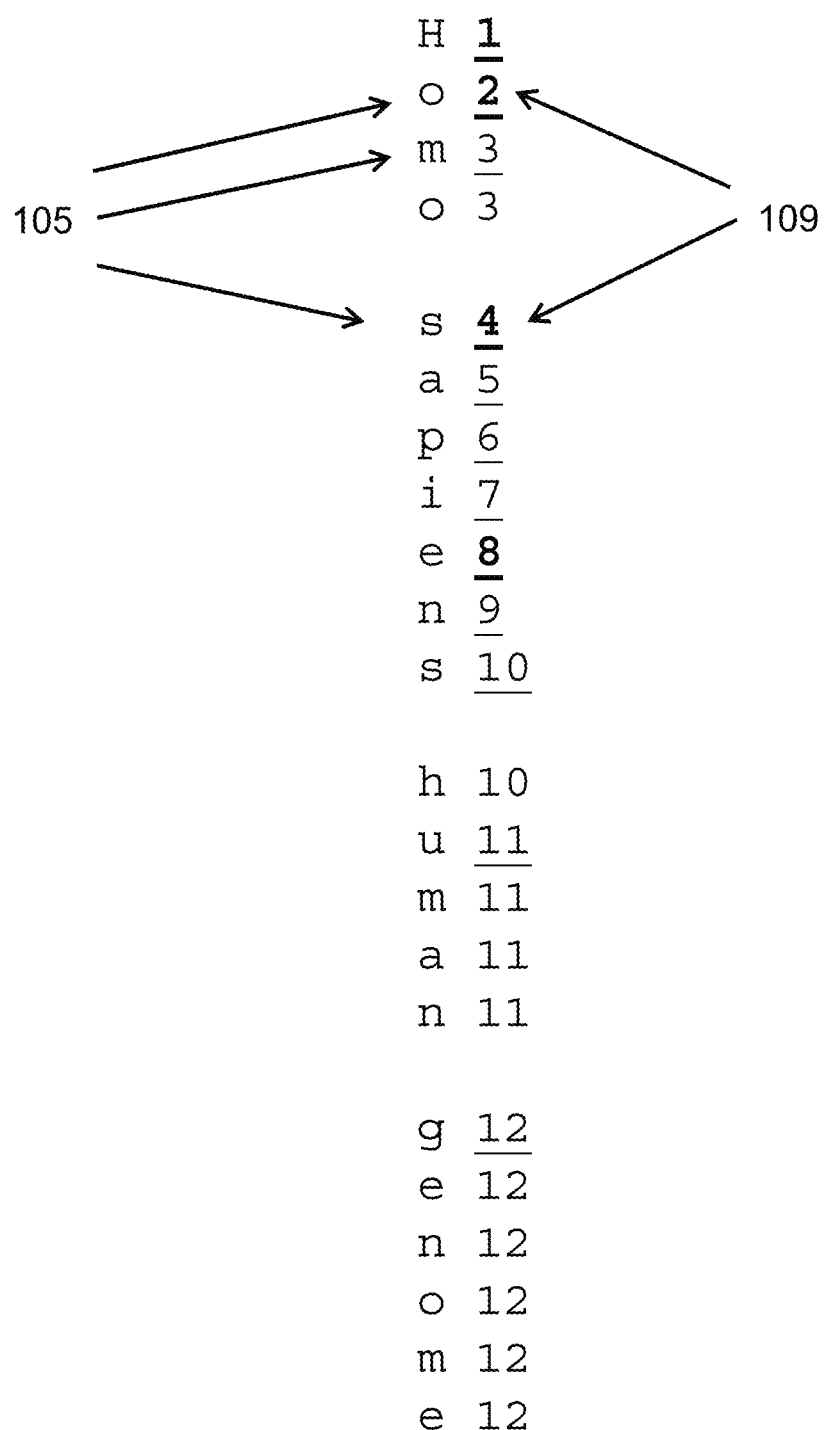
FIG. 10 illustrates changes in alphabet size along a sequence of characters.

FIG. 10 shows an exemplary interleaved metadata sequence: "*Homo sapiens* human genome". Similar to encoding of a nucleotide sequence (as shown with respect to FIGS. 2-3), as the system scans along the sequence, the system identifies 105 points along the sequence at which alphabet size will change and notes 109 those points at which the alphabet size will increase to a power of two (e.g., go from 3 to 4 or from 7 to 8). The string of numbers in FIG. 10 gives—for each position—the number of characters required to represent the sequence up to that position. The underlined positions indicate where the number increases. These numbers that are boldface denote 109 the powers of two. The powers of two are the relevant break-points for the preferred embodiments, because the fact that constant-length encoding will be used in the next stage means that all numbers of characters between $2^N+1$ and $2^{(N+1)}$ will require the same number of bits per character to encode. Whenever one of these relevant break points is encountered, the system may calculate how much space it would take to encode the sequence with an alphabet of that size. The efficiency of the representation is then calculated, and these efficiency figures can be compared in order to determine the best alphabet size for a given region, thereby choosing the break-points that optimize 113 the compression.

Any suitable method can be used to choose the breaks that optimize 113 the compression.

One reasonable rule to apply at this stage is that if a given alphabet size is more efficient than the next two larger alphabet sizes, that alphabet should be used, and the process should be re-started after that section. So, for example, if the efficiency calculated at the location corresponding to 2 is better than that at the locations corresponding to 4 and 8, it is to be used, and the process begins again at the next location. With the optimal break-points selected, the system then divides 119 the text into segments and encodes 319 each segment.

FIG. 11 shows an exemplary historical LRU-list 1101 of alphabets used by metadata according to certain embodiments. As described previously in FIG. 6, the LRU-list may be a dynamic list of the sixteen most recently used alphabets, where sixteen is an adjustable parameter of the method. Whereas the alphabet depicted in FIG. 6 is comprised of nucleotides (e.g., as in genomic sequence data), the alphabets shown in FIG. 11 are representative of metadata that may be associated with genomic sequence data, and can be encoded via DAC.

Advantages of DAC

Several advantages of the DAC technique have been mentioned or result from the disclosed systems and methods. The DAC technique compresses and decompresses not only efficiently but quickly: In an initial implementations on a laptop, encoding at roughly 100-500 Mbps and decoding at roughly 1-2 Gbps was achieved. The DAC technique has good applicability to bioinformatic data and may be applied to arbitrary alphabets of up to 256 symbols (and can be further extended), and therefore for a huge variety of data.

Using this technique, bioinformatic data may be compressed more efficiently than if one were able to encode every nucleic acid with two bits.

The technique supports fast random data access. Although the details of random access can vary, one efficient scheme involves keeping track of the locations of each of the blocks of data used in the DAC encoding. A location can then be represented with the ordinal location of the data block and the offset of the position within that data block. The first of those two numbers will range from 1 to K, where K is the number of data blocks in the DAC representation. The computational cost of random access will therefore be, on average, O(log 2(K)+(N/K)); the first term represents the cost of doing binary search on the K data blocks in order to find the right one, and the second one represents the cost of finding the beginning of the data block; this approximate average cost of this sequential search will be one-half of the average length of a block, which is N/K, where N is the total length of the sequence.

In a preferred embodiment, random access is supported by including a table containing a limited number of pairs <offset in original data, offset in data representation stream>. For example, <1000, 345> means that 1000th symbol of original data is the first symbol in encoded block which starts at position 345 in the encoded stream. So, to decode this symbol, the system jumps to 345th position in the encoded stream and starts decoding the block (it is guaranteed that these offsets correspond to the first positions of block headers; moreover, these entry blocks are blocks for which LRU alphabet tracking is being re-set). The first symbol of the block being decoded will be the symbol the system is looking for. To decode 1005th symbol, the system jumps to 345th position and starts decoding, but in this case skips the first 5 decoded symbols. If the random access entry points are distributed approximately evenly, so that the distance between 2 neighbor points is about the same, say, M, then M/2 symbols will be skipped on average. For N data symbols and K entry points, M/2=(N/K)/2 points will be skipped. To determine the entry point requires log 2(K) operations. The entry points cannot be distributed evenly in reality, because they correspond to the start position of encoded blocks and these blocks have arbitrary sizes. To address this, the system applies some binary search first to find the closest preceding entry point, which is log 2(K) in terms of complexity.

Application to Graph Genomes

One particularly useful application of the DAC approach is for storing nucleotide data and metadata associated with graph genomes, which are multi-dimensional structures incorporating genomic information from a plurality of individuals. Due to the quantity of nucleotide sequence associated with a graph genome (or chromosome, or any graph reference that describes genomic variation), DAC can compactly and efficiently store associated nucleotide data and metadata in a format allowing for ease of data analysis and transfer.

Genome sequencing is an active field of research. Sequencing genomes allows for a better understanding of human genetic variation, the influence of genetic variation on predisposition to disease, and the effectiveness of responses to therapy. Aided by recent advances in DNA sequencing technologies, the costs for sequencing whole genomes have plummeted. But with this advance has come an explosion of data. The current version of the human genome (GRCh38/hg38) is about 3.2 billion nucleotides in length. When represented on a computer, this occupies about $6*10^9$ bytes. As the number of sequenced genomes in an analysis increases, analyzing and comparing genomes quickly becomes intractable, especially when computational resources are limited.

One way to efficiently represent and manage information from multiple genomes is to only consider variations from a base reference. For example, after sequencing an individual's genome, one may store only those differences from the reference, including single nucleotide polymorphisms (SNPs), small insertions and deletions, and other structural variants. One way to store only differences from a base reference is to represent variants as edges in a directed graph. In such a graph, a base or backbone branch represents a reference sequence, such as a chromosome. Each variation from the reference sequence may then be included as an additional directed edge specifying a path diverging from the base branch. Representing genomes as directed graphs has particular benefits when used with next generation sequencing and alignment, because variations are already accounted for within the graph.

In use, sequence reads are aligned to edges or paths through the reference graph, and then genotyping can be performed by counting the number of reads across each path or by identifying mismatches across each path. Because the sequence reads are aligned to the reference graph which includes known variation, the subsequent step of identifying mutations by comparing to a table of known mutations can be eliminated. Further, alignment to reference graphs results in greatly improved results for larger structural variants, as well as indels and SNPs located near structural variants. Additionally, in some cases, there may be no need to perform an additional variant calling step because an ideal reference graph will not have any mismatches from the sequence read (of course, variant calling can still be performed to detect unknown variations).

Despite these advances, the size and complexity of graphs representing large genomes with many variations (e.g., for thousands of cancer patients) may grow to a point in which both storage and performance considerations become limiting factors. The number of people having their genomes sequenced and the associated data may grow the size of the graph to a point where storage costs become prohibitive. Further, as the graph becomes larger, the increased time required to store, query, and manage the graph may affect the ability to perform meaningful research. Accordingly, DAC can be applied to efficiently encode data stored in reference graphs, rendering them more useful and portable.

Figure 12:
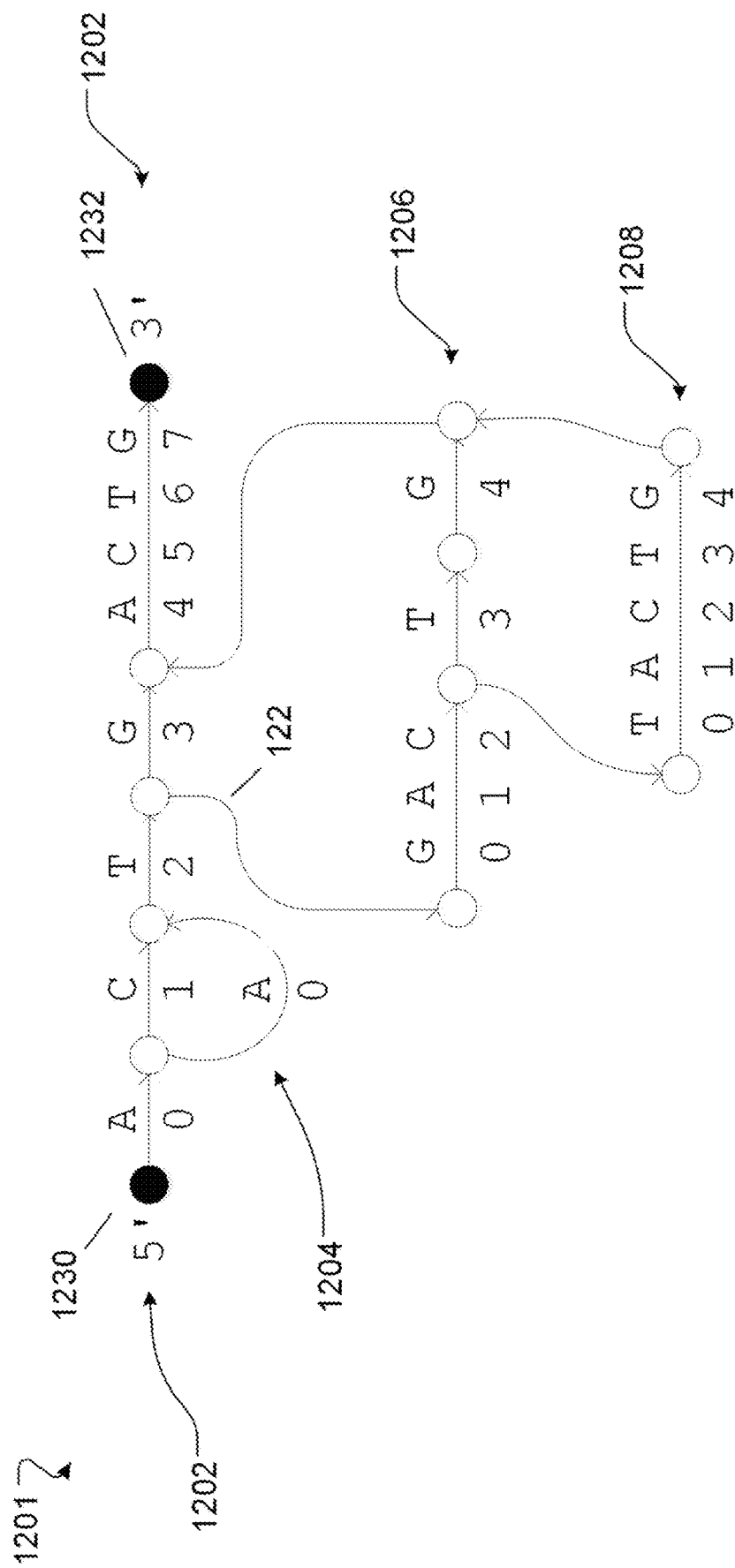
FIG. 12 depicts an exemplary genomic graph.

FIG. 12 depicts an example of a reference graph 1201. The reference graph 1201 can be a directed graph that depicts known variation in a reference genome. As shown in this embodiment, the reference graph 1201 associates nucleotide sequences with the edges (and thus is an edge-based representation). Similarly, edges may have associated metadata (not shown) describing properties of the nucleotide sequence of that edge. Edges in the graph 1201 are connected by a plurality of vertices. At each vertex, there may be one or more outgoing directed edges specifying the possible paths that may be followed from that vertex. A series of distinct outgoing edges connected by vertices may be referred to as a branch. (Similarly, the term "path" may describe a particular series of outgoing edges connected by vertices, which may span multiple branches.) Each letter in the nucleotide sequence may be associated with an offset, which is an integer specifying the relative position of the letter within the branch. In other words, along a given branch, the offset starts from "0" (at the first nucleotide) and increases by "1" for each successive nucleotide. In the described examples, the offsets are zero-based. However, other offset values or even coordinate systems may be used.

Often, reference graphs designate a backbone branch representing a particular linear reference sequence (e.g., the nucleotide sequence of chromosome 1 of the human genome).

Additional branches diverging from and reconnecting to the backbone branch thus represent known variation from the linear reference sequence, and represent events such as single nucleotide polymorphisms ("SNPs"), small insertions and deletions ("indels"), and larger structural variants. As shown in FIG. 12, the graph 1201 comprises a backbone branch 1202 having 5 edges which, when read sequentially in the direction associated with each edge, represents the nucleotide sequence "ACTGACTG" (SEQ ID NO. 6). Each nucleotide in the sequence is associated with an increasing offset value (0, 1, 2, etc.) indicating its relative position along the branch. Further, the backbone branch 1202 has two special vertices: a source vertex 1230, designating the first vertex in the graph 1201 and the 5' end of the associated nucleotide sequences; and a sink vertex 1232, designating the last vertex in the graph and the 3' end of the associated nucleotide sequences.

The reference graph 1201 includes three additional branches specifying variations from the backbone branch 1202. For example, a first branch 1204 represents a nucleotide sequence "A", a second branch 1206 represents a nucleotide sequence "GACTG" (SEQ ID NO. 7), and a third branch 1208 represents a nucleotide sequence "TACTG" (SEQ ID NO. 8). As shown, the first branch 1204 and the second branch 1206 are each connected to the backbone branch 1202, and the third branch 1208 is connected to the second branch 1206. Similar to the backbone branch 1202, a nucleotide sequence for each of the branches 1204, 1206, 1208 is associated with an increasing offset value starting from zero.

Each branch describes a path or a particular set of edges and vertices within the reference graph 1201 that may be followed through a series of increasing offset values. While the branches 1202, 1206, and 1208 (and offsets) are shown at specific locations relative to the backbone branch 1202, these or other branches could be specified in a variety of ways. For example, the backbone branch 1202 could instead begin with "AAT" instead of "ACT". In that case, the edge representing the nucleotide "A" in 1204 would instead be reassigned to the backbone branch 1202, with a corresponding reassignment of the offset values as well (i.e., the edge within branch 1202 that specifies "C" would instead be assigned an offset of "0" as a new alternate branch, whereas the edge specifying "A" would have offset "1" in the backbone branch). Accordingly, for a particular graph, designated branches and offset values may vary.

In practice, designating offsets and branches may be specified as a graph is created. The first reference sequence incorporated can be specified as the backbone branch, and its associated nucleotide sequence can be assigned increasing offset values. Subsequent sequences representing variations from the reference can be inserted as new branches connected to the backbone branch. These new branches will have new relative offset values starting from zero.

While the reference graph 1201 shown in FIG. 12 includes only several short nucleotide sequences, reference graphs can be much larger. For example, a reference graph may include information from an entire population, allowing for the characterization of genetic variants with unprecedented accuracy. In such reference graphs, the associated nucleotide data may exceed millions of bases. Accordingly, DAC can be applied to nucleotide data in order to render the reference graph portable.

Figure 13:
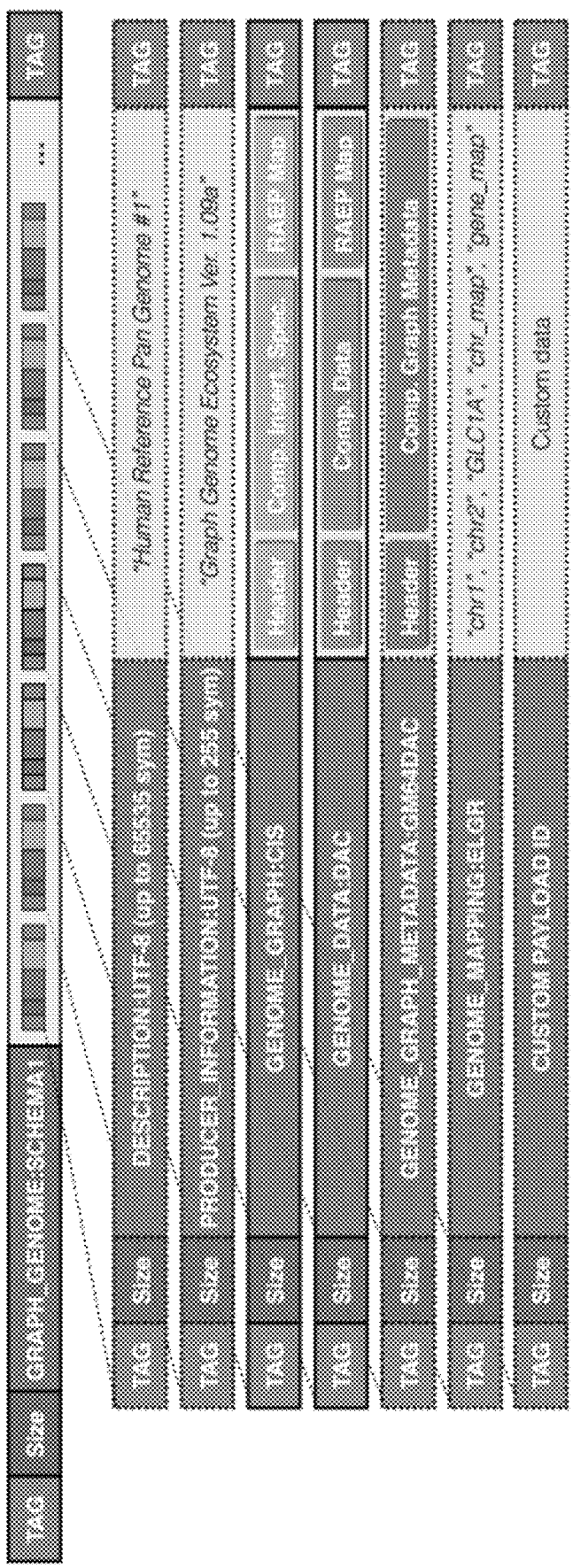
FIG. 13 diagrams a containerized, fully encoded genomic graph.

Reference graphs can be stored in a variety of formats. FIG. 13 diagrams a full encoding of a genomic graph (such as the reference graph 1201) in which nucleotide sequences are associated with edges. It is noted that the graph is containerized and that each row in FIG. 13 represents a container. A genomic graph may be containerized according to a Graph Genome Compression and Serialization (GGCS). The GGCS may include containerization of data. Using a containerization schema of the invention, data are represented by a sequence of containers. Preferably, the containers are intrinsically linear in that a container defines a sequence of regions each of which contains a sequence or string of data.

Any suitable containerization scheme may be employed. In the depicted embodiment, each container includes five regions: an opening tag, a size region, a type region, a data region, and a closing tag. The opening tag could be any agreed-upon sequence that marks the beginning of a container. The size region contains the actual size of the container (not, for example, the maximum size permitted for a container of that type). The type region indicates the type of data held in the container (for examples, see the description container, producer information container, graph geometry information container, graph content container, graph metadata container, genome mapping container, and custom field container all discussed below). The data region contains the data of the type indicated in the type region. The closing tag could be any agreed-upon sequence that marks the closing of the container. Containers may be implemented in any suitable format. In some embodiments, containers are created in extensible markup language (XML). A containerization scheme according to the invention has recursive potential. For example, containers can contain other containers in the data region, so container-types can be more complex. For example, the data region of any one container may include one or multiple other containers.

A containerization scheme according to embodiments of the invention has the ability to generate sub-schemas. Rules can be created or added further constraining the number, type, and order of containers, which can be useful in a given domain. GGCS1, described below, is one such sub-schema.

A containerization scheme according to the invention has linearity and compression-friendliness: containers are intrinsically linear, and they contain sufficient information about their own sizes and data to facilitate compression and transmission.

In one embodiment of a method for the containerization and serialization of graph genomes, dubbed GGCS1, a particular subschema of the containers is employed. The subschema may include the requirement that a container includes separate but related containers for the geometry and content (i.e., nucleotide sequences) of a genomic graph such as the directed graph 901.

In FIG. 13, the dashed lines indicate positions within the top-listed, or "outer-most", container wherein each of the following container are nested.

In the first sub-container, the type region reads "Description: UTF-8" and the data region reads "Human Reference Pan Genome #1".

In the second sub-container, the type region refers to producer information and the data region refers to a graph genome ecosystem.

In the third sub-container, the type region identifies that the type includes graph geometry and the data region includes a representation of a geometry of the graph. A suitable representation is described in U.S. patent application Ser. No. 14/885,192, filed Oct. 16, 2015, titled Biological Graph or Sequence Serialization. U.S. patent application Ser. No. 14/885,192, filed Oct. 16, 2015, and any pre-grant publication and any patent that issues therefrom are hereby incorporated by reference.

In the fourth sub-container, the type region shows that the container includes genome data (here, encoded by DAC) and the data region includes the genome data.

In the fifth sub-container, the type region shows that the container includes genomic graph metadata, and the data region includes the genomic graph metadata. The genomic graph metadata is preferably encoded according to the methods and systems disclosed herein, e.g. by DAC.

LFPR8/LR8 Encoding

One way to efficiently encode graph-related data is by variable length encoding. A variable length code is a code which maps source symbols to a variable number of bits. For example, a variable length code to store integers associated with sequence data or metadata components from a reference graph could simply store only the bits required. However, this can be troublesome because a decoder will then require prior knowledge of the number of bits required for each component, which introduces additional overhead costs that may negatively impact the encoding scheme. Moreover, most operating systems expect binary data to be represented in bytes, i.e., as 8-bit octets. Deviating from this norm can lead to problems and confusion during development of software that uses a graph coordinate system. The present disclosure recognizes that these problems are solved by an encoding scheme that represents sequence data (and in some embodiments, metadata) as a variable number of bytes, wherein the representation itself includes information about its size. In particular, an encoding scheme for storing sequence data is proposed in which a header octet indicates the number of additional bytes ("Length") following the header octet that are used to accommodate the stored information ("Representation"). In this way, the encoding scheme is able to minimize the number of bytes required to store sequence data, thus achieving efficiencies in storage and speed while also not suffering from problems associated with pure variable length encoding schemes. Further, the header may also store other information related to the sequence data (e.g., the alphabet to be used) as additional binary information, such as a set of flags ("Flags"). We refer to this novel encoding scheme as LR8 (Length—Representation—8-bit octets) or LFR8 (Length—Flags—Representation—8-bit octets) encoding. The LFR8/LR8 encoding schemes can be used to efficiently encode any kind of data, including graph-related and sequence-related data.

FIG. 14 diagrams an encoding process 1400. A computer system scans an integer, and determines 1402 the number of bits sufficient to represent the integer. A computer system then encodes 1404 the integer using the determined number of bits and generates 1406 a header value that indicates the total number of octets representing the encoded integer. The header value may be embedded together with the encoded integer. Optionally, auxiliary information (flags) can also be encoded.

In an embodiment, the data is divided into two parts: header values and a data representation. The header values and data representation can be considered to be an LFR8 word. The header provides information about the length of the data representation and allows the data representation to be interpreted accurately. A computer system may be programmed with instructions that when executed by a processor cause the system to interpret the header and use that information to decode the data. In certain embodiments, the header is encoded according to a scheme that depicts a length of what is encoded, certain useful flags, and the encoded representation, all using 8-bit octets (where the encoded representation here will be a length of the data section, such as the number of octets following the header octet). Thus, methods and systems of the invention implement a length-flag-representation 8-bit scheme.

Figure 15:
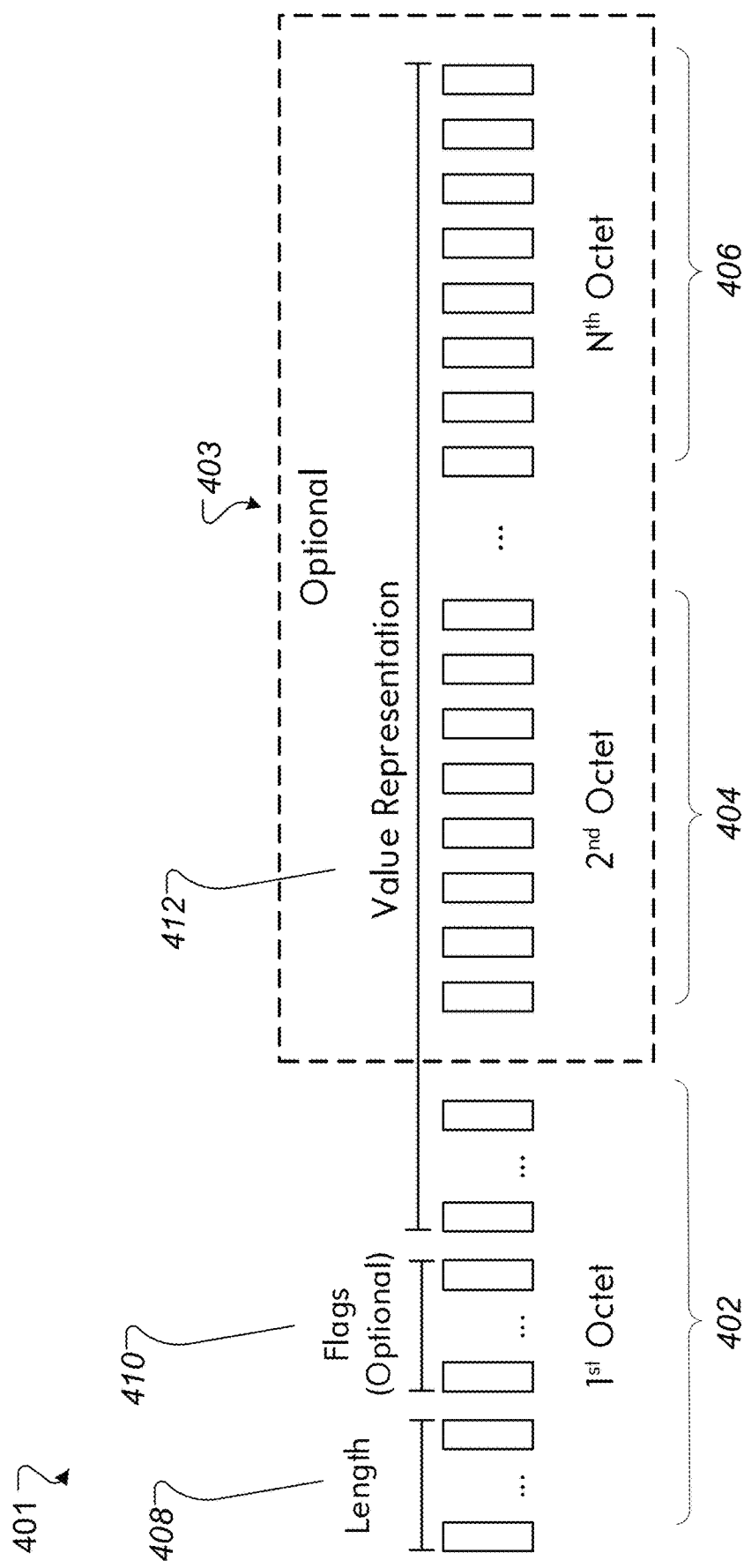
FIG. 15 shows a representation of encoded information using an embodiment of a variable length encoding scheme (e.g., a length-flag-representation-8 bit octet (LFR8) encoding scheme).

FIG. 15 shows a representation of encoded information 401 using a variable length encoding scheme (e.g., a length-flag-representation-8 bit octet (LFR8) encoding scheme). As previously described, the proposed scheme can be used to serialize information about sequences and metadata within a graph. In this example, the data is divided into a series of octets. A first octet 402 defines a length 408 of the encoded information 401. For example, the length 408 indicates the number of octets (or bytes) following the first octet 402. In some cases, the first octet 402 is also referred to as a header octet. The first octet can optionally also include additional bits of information (e.g., auxiliary binary information), which can function as flags 410. In some cases, these flags can indicate the context of the encoded integer. For example, a flag can be used to indicate whether the sign of an integer is negative or positive. Similarly, flags can be used to indicate how an encoded DAC representation should be decoded.

If the first octet 402 has available space (e.g., as shown in FIG. 15) not occupied by length bits or flag bits, the first octet 402 can also include a portion of the bits required for value representation 412, i.e., data bits representing the binary form of the encoded integer. By using any available space within the first octet 402, the use of available space is maximized. Similarly, if the available space in the first octet 402 is insufficient to represent all of the data bits, then the first octet can be followed by additional octets 403. For example, the encoded information 401 can also include a second octet 404 . . . to an Nth octet 406 to represent all of the data bits in the value representation 412.

As shown in FIG. 15, the first octet serves as a header that defines the number of octets (bytes) following the 1st octet. The header octet may also include additional bits serving as flags which can indicate the context of the encoded integer. The representation of the integer in binary form then follows. If not all bits are used in the header octet, then the header octet may also include some value representation bits, thus maximizing usage of available space. Similarly, if the number of representation bits available in the header is insufficient to represent the value, then the header is followed by a sequence of additional value representation bytes.

Further, as previously described with respect to FIGS. 4A-B, in the DAC format, an LFR8 encoded integer can describe the section length of the encoded text. Further, in the DAC format, the flags associated with an LFR8 encoded integer can describe the alphabet representation to be used to decode the encoded text. Accordingly, the DAC technique leverages the LFR8 format to create a larger data structure in which an LFR8 encoded integer can be interpreted to also define an alphabet and a subsequent data representation (e.g., encoded text).

The LFR8/LR8 encoding schemes can be used to efficiently encode any integer. In particular, when applied to graphs, the proposed format results in structures that are efficiently encoded and byte-aligned, allowing for easy processing and integration into workflows and other software tools. Further, the data has been encoded in a way that is efficient in terms of both compression ratio and time, but is also lossless in terms of information accuracy.

A specific example is discussed.

Consider the position 4,954 on a reference genome. When represented in binary form, this position becomes:
1001101011010

The binary form of this integer requires 13 bits, and thus requires at least two octets, of which three bits are unused in one octet.

Figure 16:
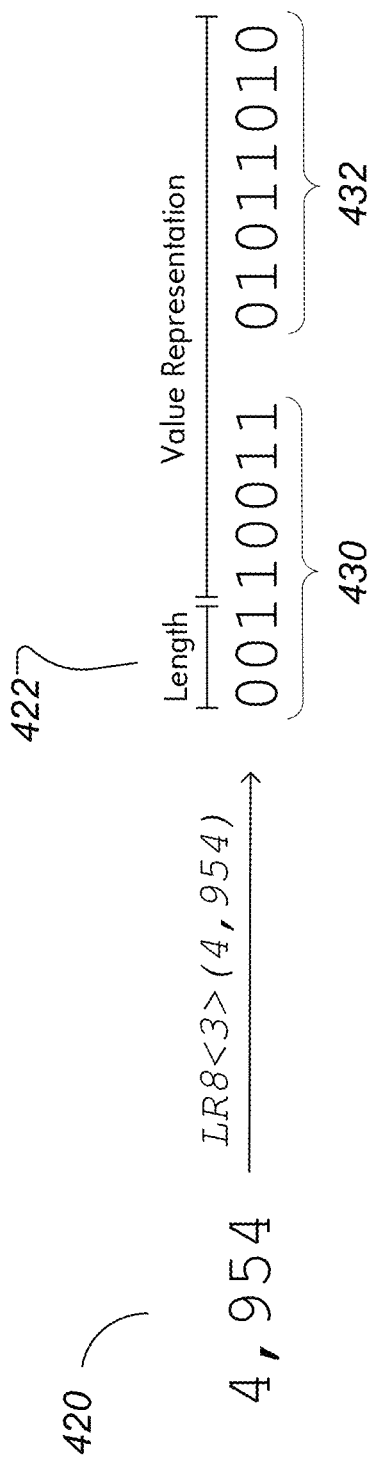
FIG. 16 shows an encoding of an integer, "4,954", in a length-representation-8 bit (LR8) encoding scheme where three length bits in a header octet represent a header value.

FIG. 16 shows an encoding of a coordinate value 420 (as shown, the integer "4,954"), in a length-representation 8-bit encoding scheme where 3 bits in a header octet represent a length value. For example, when represented in binary form, the coordinate "4,954" on a reference genome becomes 1001101011010. The binary form requires 13 bits, and thus requires, at least, two octets, of which three bits are unused in one octet. LR8<3> refers to LR8 format using three (3) length bits in the header octet. The remainder of the header octet is then available for storing the representation of the value, i.e., the encoded integer. As shown in this example, the encoded representation in LR8<3> format comprises two octets: a header octet 430, and a value representation octet 432. The three length bits 422 in the header octet indicate that there is one additional octet in the representation ("001"). Based on the size of the encoded coordinate, the value representation parameter of the encoding scheme can be selected to accommodate the number. A user or a computer could identify the range of numbers expected to be encountered in a particular application, and then select an appropriate value representation parameter that is large enough to accommodate that number. For example, the number of length bits used by the format can vary, e.g., LR8<4> format, LR8<5> format, and so on.

Figure 17:
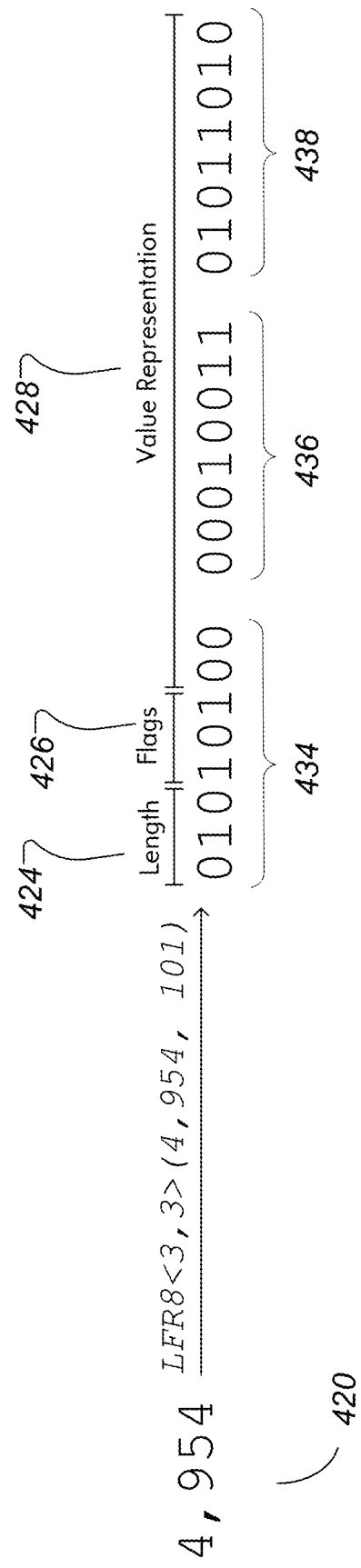
FIG. 17 shows an encoding of an integer, "4,954", in a length-flags-representation (LFR8) encoding scheme where three length bits in a header octet represent a header value and three length bits in the header represent auxiliary binary information (e.g., a set of flags).

FIG. 17 shows an encoding of the coordinate value 420 ("4,954"), in a length-flag-representation 8 bit (LFR8) encoding scheme where three length bits 424 in a header octet 434 represent a header value and three flag bits 426 in the header represent auxiliary binary information (flags). (This leaves an additional 2 bits available within the header octet, which may be used by value representation bits 428). In some instances, it may be desirable to include additional binary information within the encoded representation of the integer, e.g., as a set of flags. Flags can be included in the header octet using LFR8 format after the length bits. Sometimes, there is a need to store additional flags with a position. The encoding scheme parameters can be adjusted to accommodate these bits. In these cases, the flag information can be encoded as flag bits 426 (e.g., "101"). As shown in FIG. 17, the encoded representation comprises three octets: a header octet 434, and value representation octets 436, 438. Three flag bits 426 occupy additional bits in the header, leaving insufficient bits available to store the coordinate value 420 ("4,954") in only one additional octet. Accordingly, two ("010") additional octets are required for the LFR8 representation.

As shown in FIGS. 16-17, the number of length bits and flags may be provided as a parameter, such as by LR8<X> or LFR8<X,Y>, wherein X represents the number of length bits and Y represents the number of flag bits. The actual value to be encoded and flags may also be provided as secondary parameters, such as by LR8<X> (Value) or LFR8<X,Y> (Value, Flags). Accordingly, the LFR8 and LR8 encoding schemes can be written as a function that encodes and outputs an integer value and a set of flags as a variable number of bits. In this way, the disclosed encoding schemes describe a highly efficient, yet lossless, means for compressing data related to graph coordinates, paths, and positions.

Once encoded, a decoding agent or algorithm would receive the first octet of an encoded integer and then determine, based on information within the first octet, the total size of the representation.

The proposed LFR8/LR8 encoding scheme provides a graceful solution for storing integers that both efficiently encodes integers but is also easily manageable. The scheme efficiently represents a value with a descending probability distribution and including auxiliary binary information (e.g., a set of flags), which can serve to identify the particular coding context used. Further, the encoding scheme presents a good compromise between encoding and decoding complexity and coding efficiency by using variable lengths, yet providing byte-aligned code, providing no need for additional padding. Parameters can be adjusted to fit any application. Further, strings of LFR8/LR8 encoded integers can be placed in sequence and have different parameters, allowing for complex data structures and coordinates to be defined.

Modifying the Encoding Schemes

In the encoding schemes discussed above (e.g., LFR8 and LR8 formats), the total number of length bits and flag bits does not exceed eight so that the header information remains within a first octet. If some bits are unused, these bits can be allocated to any position within the encoded representation. In the examples described above, the value representation is shifted to the rightmost position of the octets such that the last bit in the last octet is the first bit of the encoded integer. However, these value representations can be shifted in a different position or permuted in a different manner.

Any unused bits (i.e., to the left of the value and after the length and flag bits) may be padded as zeros. However, the LFR8 and LR8 formats could be modified to use additional header octets to store additional flags as needed. Similarly, flags could also be stored in the additional representation octets (e.g., LFR8<3,6> would require at least one flag bit in an additional octet).

As previously described, an LFR8 format is compatible if the particular application requires storage of additional flags. In these cases, encoding an integer may require an additional octet because there will be additional flag bits in the header. For example, encoding the integer "4,954" requires only two or three octets, depending on whether LR8 or LFR8 format is used. For example, a position 201,348,366 on human chromosome 1, represented in binary form, becomes: 1100000000000101010100001110. The binary form of this integer requires at least 28 bits, and thus requires at least four octets in order to be byte-aligned (32 bits), of which half of one octet is unused. When stored using LFR8 format, the header octet that includes the value representation begins with "011", indicating that three additional octets follow the header octet.

The encoded representation, including the length (L), padded bits (P), and binary value (V) thus becomes:

| LLLPVVVV | VVVVVVVV | VVVVVVVV | VVVVVVVV |
|---|---|---|---|
| 01101100 | 00000000 | 01010101 | 00001110 |

If flags are desired, the encoding scheme can also accommodate flags (F), for example, following the length bits. In this case, if we would like to include four flags in the header octet, we would require five octets, as the binary value of the integer is then shifted to the right, as shown in the example below:

| LLLFFFFP | PPPPVVVV | VVVVVVVV | VVVVVVVV | VVVVVVVV |
|----------|----------|----------|----------|----------|
| 10010110 | 00001100 | 00000000 | 01010101 | 00001110 |

Padding (e.g., "0" bits) can be used when there are unused bits in the representation. Of course, these bits can be used to store additional binary information (e.g., up to 5 binary symbols or flags if three representation bits are used). For example, if we need to store 3 flags, we can convert the LR8<3> schema to LFR8<3,3>, e.g.:

| LLLFFFPP | VVVVVVVV |
|----------|----------|
| 00101100 | 10011010 |

This particular encoding scheme (i.e., one in which three length bits are present in the header) allows for up to seven additional octets to be used. However, if the header octet is entirely occupied by length bits and flag bits (that is, there are no bits left over for value representation), then, in certain embodiments, the encoding scheme imposes a special rule: add at least one extra octet, and the numbers encoded in the length bits hold the number of additional value representation octets to append above and beyond this. So, for example, in an LFR8<3,5> encoding scheme, the representation would include one header octet, and the number of additional value representation octets would range from one to eight, for a total code size (including the header) in the range of two to nine bytes. Accordingly, eight additional representation octets are available in addition to the header octet, allowing for the representation of a value having $2^{64}$ positions—a value far in excess of the number of nucleotides in any presently known genome.

One reason to incorporate this special rule is so that when we encode the number "0", it does not end up being represented as a "null" value (i.e., just a header octet, with no assigned value representation bits). The reason this is useful is because if the value is changed later on, e.g., from "0" to "1", then the representation does not need to be resized in order to get the number "1" to fit. For example, imagine several million LFR8/LR8 representations, all assigned to a single contiguous block of memory. If one representation is resized by adding an extra byte, then every representation to the right would presumably have to be moved over by one byte in order to accommodate the change, which can be extremely inefficient.

When encoding, an encoder first determines, based on an integer or value to be encoded, the number of octets required for representation in a particular LFR8 or LR8 format. Exemplary pseudocode is provided below which gives one example.

```
# Invalid input: negative values should be represented
# by setting a flag bit.
if value < 0
    code_size_in_bytes = -1
else
    n_repbits_in_header = 8 - (n_lenbits + n_flagbits)
    # Hypothetically, if we used the value representation
    # bits in the header to store the least significant
    # binary digits of the input value, this would be the
    # number encoded by the remaining binary digits that we
    # would have to fit inside the variable length value
    # representation bytes.
    value_rightshifted = value / (2 ^ n_repbits_in_header)
    if value_rightshifted == 0
```

-continued
```
    # Edge case: the only way both "if" clauses are true
    # is if value == 0, but you should never represent
    # the number zero as a null, always reserve some
    # value representation bits in case we want to
    # increment later, then we don't need to resize
    # immediately.
    if n_repbits_in_header == 0
        n_repbytes = 1
    # No representation bytes needed, non-zero value
    # fits entirely in header
    else
        n_repbytes = 0
    else
        n_repbytes = ceil(log256(value_rightshifted))
    # Code size includes 1 byte for the header, plus any value
    # representation bytes, if required.
    code_size_in_bytes = 1 + n_repbytes
```

As shown in the above pseudocode, first the encoder receives a value (such as an integer) to encode. (In this example, if the value is negative, the encoder outputs an error.) The encoder then determines the number of available representation bits in the header by subtracting the number of length bits and the number of flag bits from the size of the header (i.e., 8 bits). For example, in an LFR8<3,2> representation, the number of available representation bits would be 8-3-2=3 bits. The encoder then calculates a "right shifted" value, which represents the number that would need to be encoded by the remaining binary digits once the least significant binary digits are stored in the (e.g., 3 bits of) the header. If the "right shifted" value is not zero, the encoder determines the number of representation octets required by calculating the logarithm of the right shifted value with base 256, and then identifying the ceiling (i.e., the smallest integer value greater than or equal to this value) of the result to yield the number of additional octets required for the representation. The resulting code size is thus 1 plus this number (i.e., the header octet plus the additional octets required for the representation). However, if the "right shifted" value is zero, the encoder considers whether there are any available representation bits in the header. If not (meaning that the value itself is zero), then the encoder provides for one additional representation octet. (This is to ensure that if the value itself later changes, additional octets do not need to be added; see the description of the "special rule" above.) However, if it is the case that there are available representation bits in the header, the entire representation is fit into a single octet.

FIG. 18 is a table showing how the proposed encoding scheme can be modified to accommodate both a variety of length bits and flags. The number of bits and flags may be modified as required to suit a particular application. In practice, three length bits are typically all that is needed, as this allows for storing positions far in excess of those needed for any known reference genome. Additionally, there may be many instances in which only a single octet is required for the total representation; for example, using LR8<1> format, 7 data bits would be available, which could be used to encode integers less than 27 (128) in a single octet.

Figure 19:
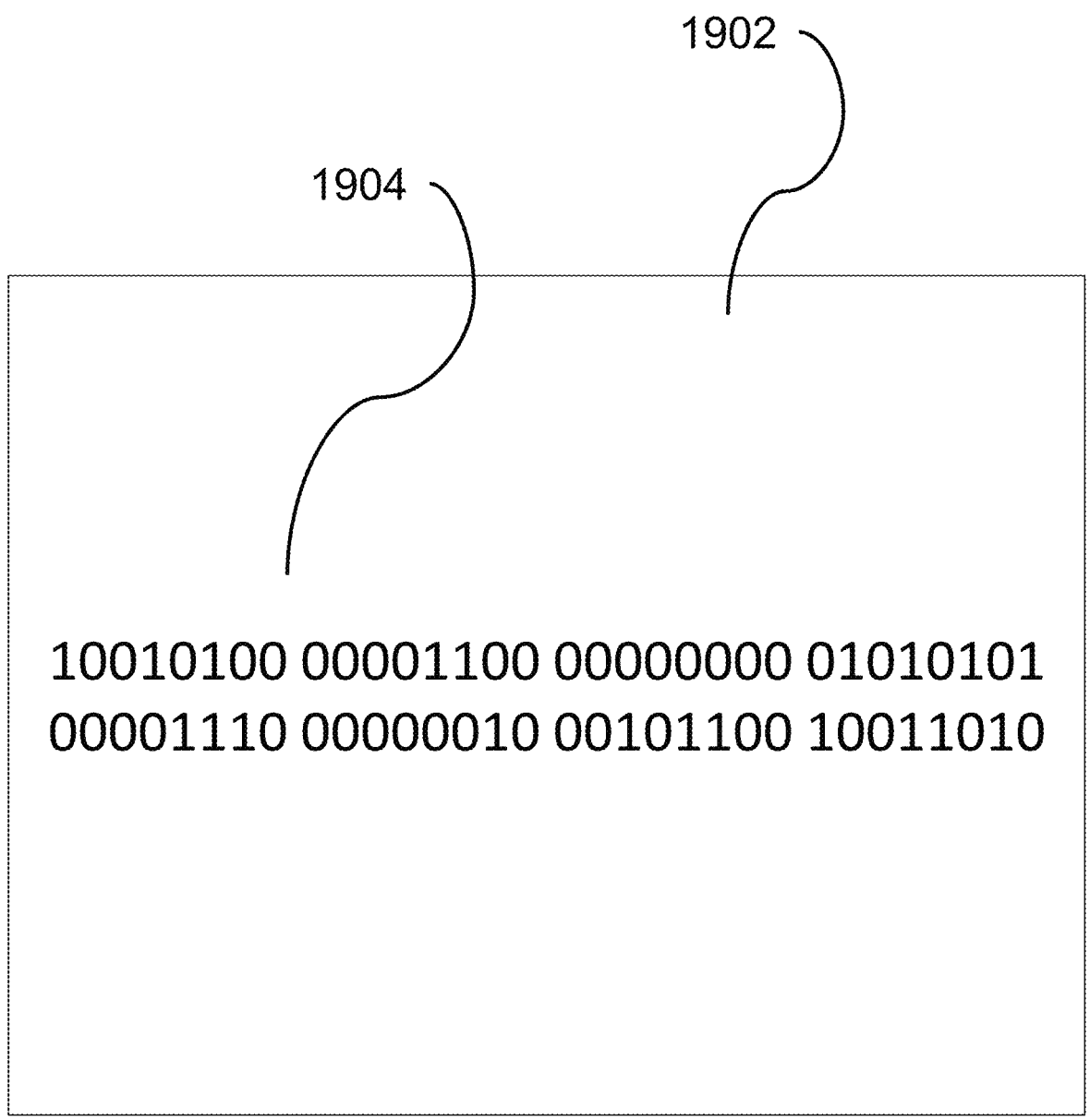
FIG. 19 illustrates an encoded set of integers that may be generated.

Note in the table of FIG. 18 the special rule previously described: if the number of value representation length bits and number of flags occupies all 8 bits of the header octet, then the value of the length bits refers to the number of additional octets in the encoded representation, giving us a total code length of between 2 and 9 bytes. In contrast, if the number of value representation bits occupies less than 8 bits of the header octet, then the value of the length bits refers to the total number of octets in the encoded representation, including the header, giving us a total code length of between 1 and 8 bytes. (However, in other embodiments, the special rule may not be applied.) FIG. 19 illustrates a report 1902 of encoded integers 1904 that may be generated by a system according to an embodiment of the disclosure. The report 1902 was generated in this illustrated example by following the process shown in FIG. 14. As shown in the report 1902, a sequence of encoded LFR8 and/or LR8 integers may be stored adjacent to one another, such that a decoder executing on a computer system can receive each octet sequentially and determine the number of octets used for each representation. In particular, the report 1902 depicts the integers "201348366", "2", and "154" encoded as a sequence of LFR8<3,3> encoded integers. Of course, in certain examples, various formats of LFR8 and LR8 integers may be used in different combinations.

Figure 20:
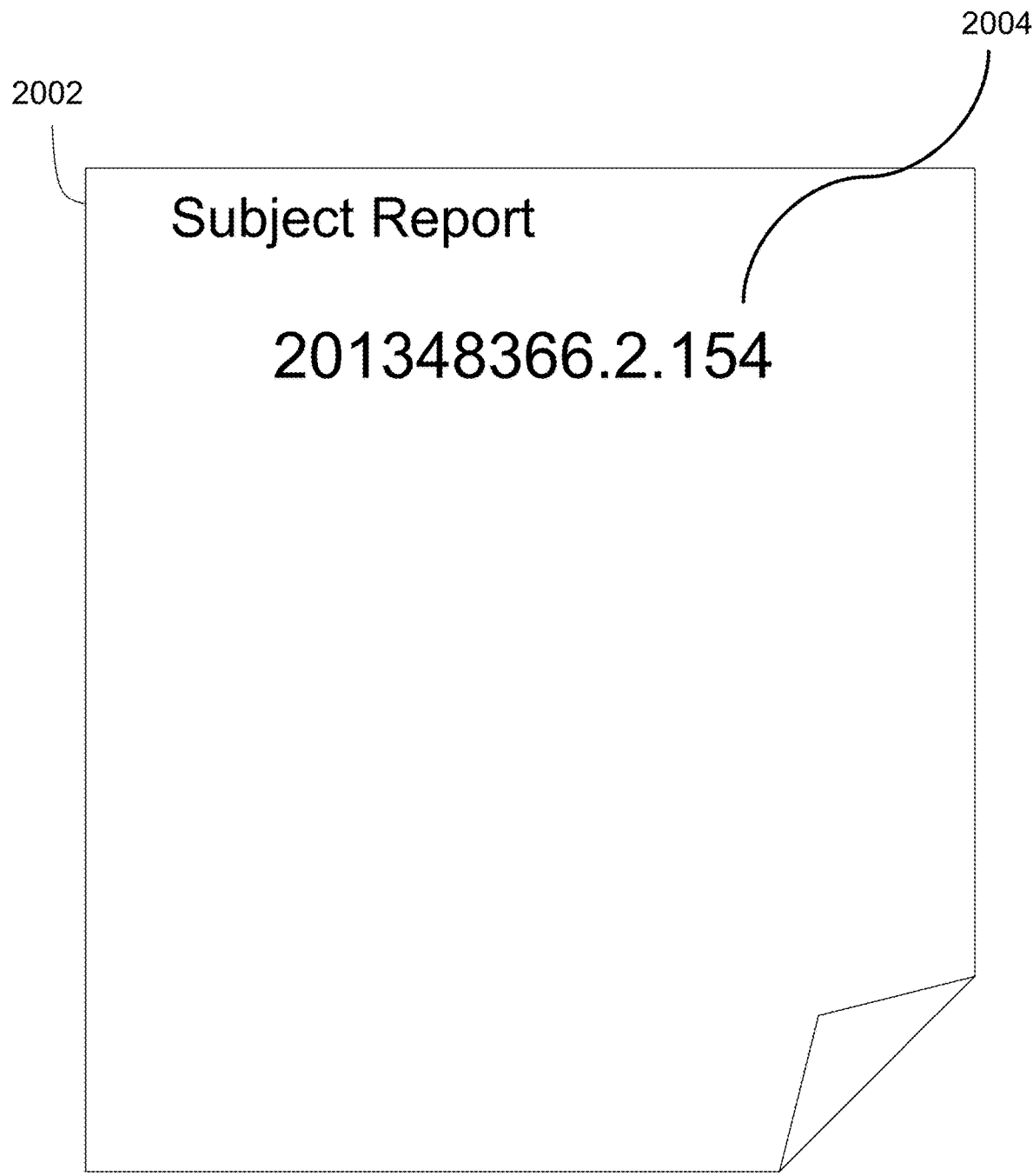
FIG. 20 illustrates a decoded set of integers that may be generated.

FIG. 20 illustrates a report 2002 that may be generated which provides decoded coordinates 2004. The report 2002 was generated by decoding the encoded integers 1904 from the report 1902 of FIG. 19, for example. A decoder can then decode the encoded integers 1904 by first receiving an octet, such as the first octet in the report 1902 of FIG. 19. The decoder then analyzes the first octet to determine the total number of octets in the current representation. The decoder then reads the total number of octets and decodes the encoded component accordingly. In some embodiments, the decoder could also determine whether the encoded component is a last component of the coordinate, e.g., based on additional or auxiliary binary information embedded within the first octet or elsewhere in the representation. As shown, the report 2002 indicates the result of decoding the LFR8<3, 3> integers from the report 1902 of FIG. 19, i.e., "201348366", "2", and "154". In certain embodiments, the report 2002 can also include a summary of the analysis resulting from such a comparison. The proposed variable length encoding schemes described herein compactly and efficiently represent a plurality of values whose frequency may reasonably be expected to follow a descending probability distribution. For example, graph coordinates will typically involve a large first component, representing a traversal to a random position in the genome (e.g., 201348366). This component can be represented using 5 octets. However, the remaining components "2" and "154" may be encoded using only 1 and 2 octets, respectively. Similarly, paths in which the second coordinate is relative to the first coordinate will typically have smaller components that can be represented using a minimal number of bytes. Accordingly, a few values will require a large number of bytes to represent; however, a large number of values will only require a few bytes. Therefore, in common with other variable length encoding schemes, the LFR8/LR8 standard achieves overall compactness of representation by assigning short code words to the most frequently used symbols or values, and longer code words to the less frequent ones.

Representative System

Figure 21:
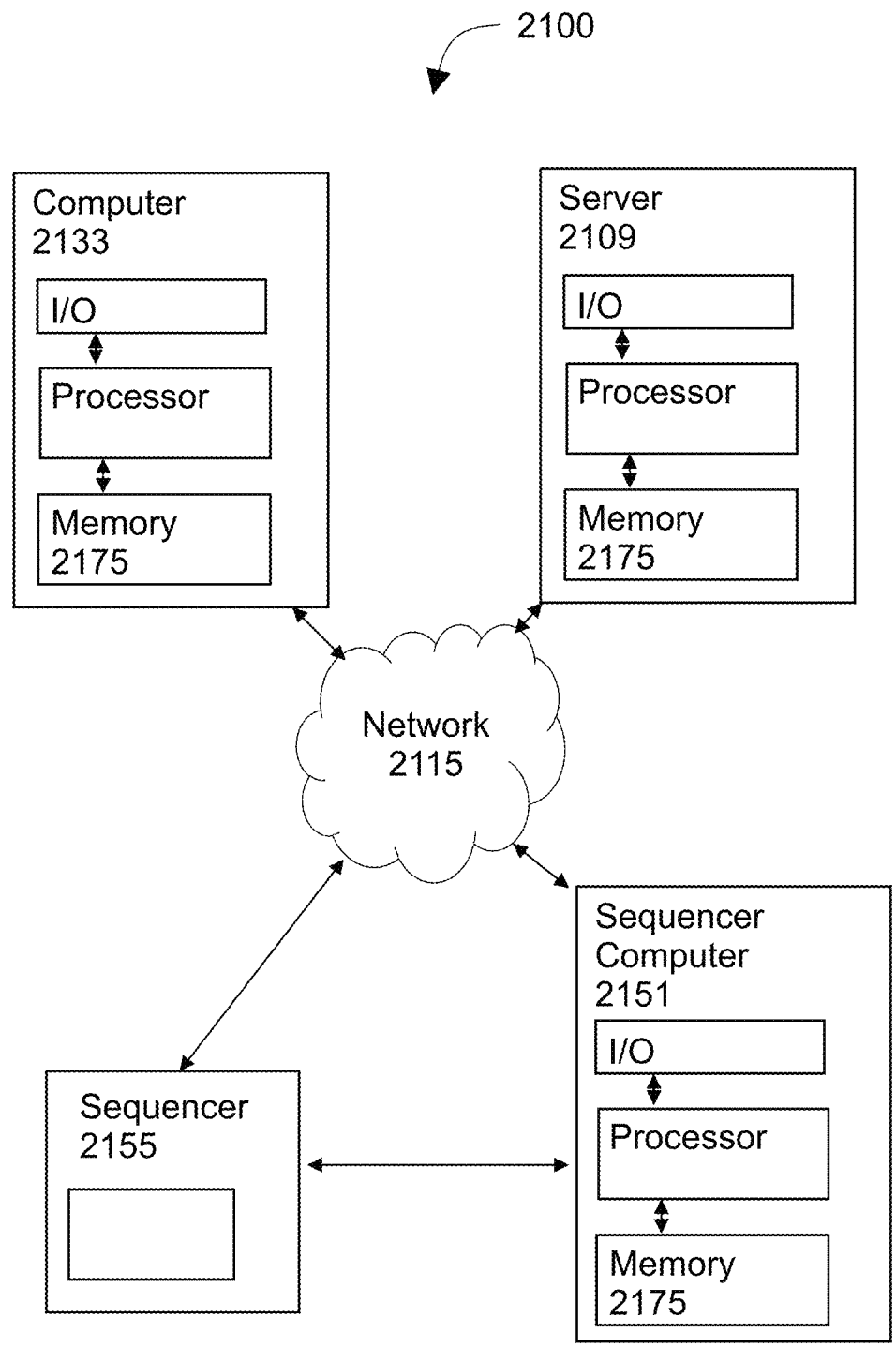
FIG. 21 diagrams a system of the invention.

FIG. 21 diagrams a system 2100 that may perform methods disclosed herein. The system 2100 includes at least one processor coupled to a tangible memory subsystem 2175 containing instructions. The at least one processor may be provided by any one or more of a computer 2133, a server 2109, or a dedicated lab computer such as a sequence computer 2151 operably coupled to a nucleic acid sequencing instrument 2155. Any of the computer 2133, the server 2109, the sequence computer 2151, or the sequencing instrument 2155 may be operably coupled to one another via a communications network 2115. The tangible memory subsystem 2175 contains instructions that when executed by the processor, cause the system to divide genomic data into a plurality of segments and encode characters within each of the plurality of segments with a smallest number of bits per character needed to represent all unique characters present in the respective segment. Within a segment, every character is preferably encoded with the same number of bits (i.e., the system implements constant-length encoding within segments).

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 2175 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 2101 is operable to divide data into a plurality of segments and encode characters within each segment using a smallest number of bits per character. The system may be initially programmed or set to operate through the use of one or more input/output device, labelled "I/O" in FIG. 21. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

In certain embodiments, the reference graph 1201 of FIG. 12 is stored in the memory subsystem 2175 using adjacency lists or index-free adjacency, which may include pointers to identify a physical location in the memory subsystem 2175 where each vertex is stored. In a preferred embodiment, the graph is stored in the memory subsystem 2175 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Sequencing Technologies

Figure 22:
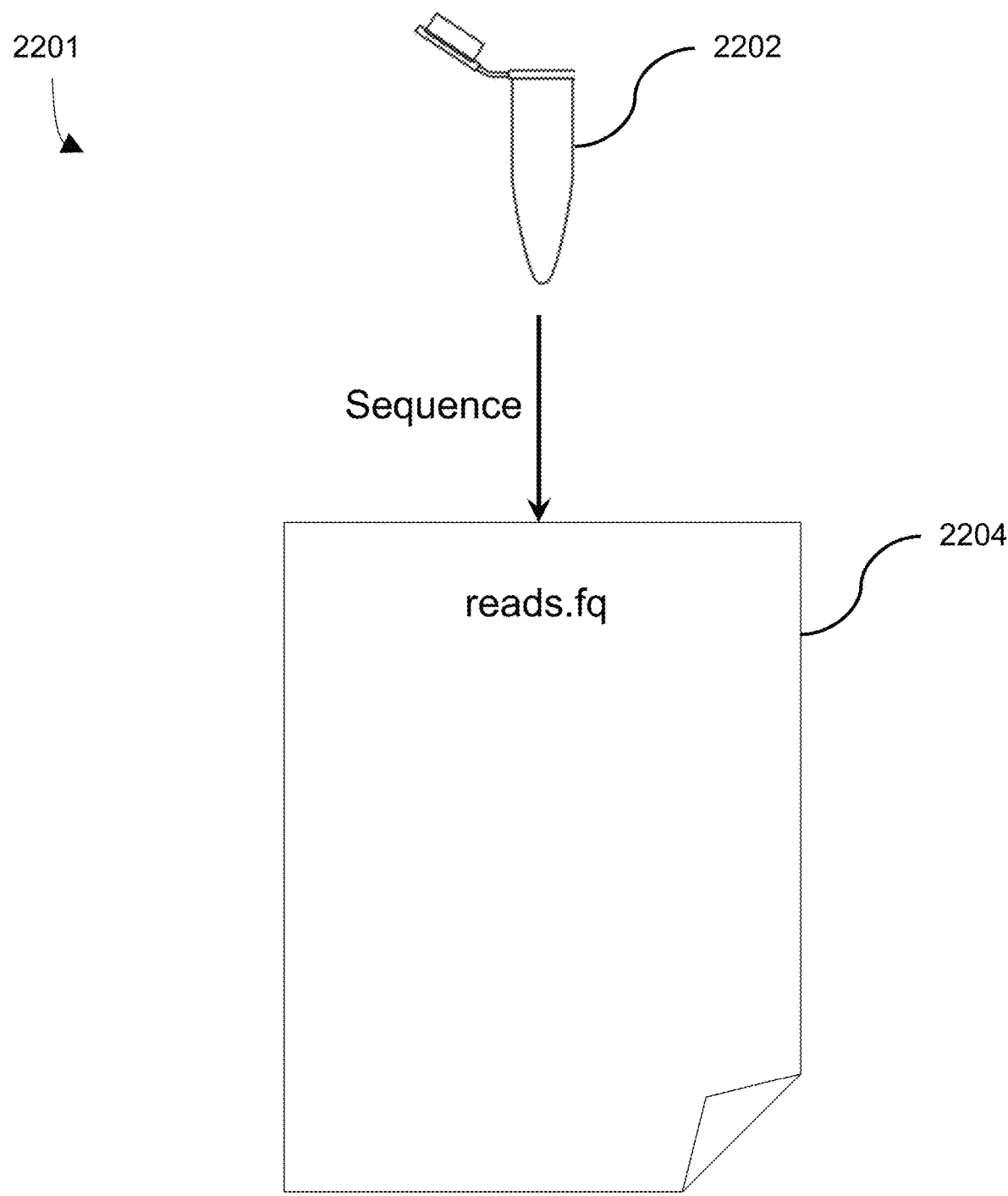
FIG. 22 illustrates generating sequence reads from a sample.

FIG. 22 illustrates obtaining 2201 a set of sequence reads 2204 from a sample 2202. As a preliminary step (not depicted), nucleic acid may be isolated and/or enriched.

In certain embodiments, sequence reads are obtained by performing sequencing on the sample 2202 from a subject (however in some embodiments, sequence reads are obtained when a read file is transferred into a system of the invention). Sequencing may be by any method and sequencing instrument known in the art. See, generally, Quail, et al., 2012, a tale of three next generation sequencing platforms: comparison of Ion Torrent, Pacific Biosciences, and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems and sequencing instruments sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024, 5,674,713; and 5,700,673, each incorporated by reference. 454 sequencing involves two steps. First, DNA is sheared into blunt-end fragments attached to capture beads and then amplified in droplets. Second, pyrosequencing is performed on each DNA fragment in parallel. Addition of nucleotides generates a light signal that is recorded by a CCD camera in a sequencing instrument.

Another sequencing technique and instrument that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique and instrument that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. The addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 22, sequencing generates a set of sequence reads 2204. Reads according to the invention generally include sequences of nucleotide data anywhere from tens to thousands of bases in length. A set of sequence reads 2204 will typically be provided in a suitable format such as, for example, a FASTA or FASTQ file. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained in a format such as FASTA, FASTQ, or similar.

In some embodiments, the sequence reads 2204 are assembled to provide a contig or consensus sequence, which contig or consensus sequence may be used in finding alignments to a reference graph. Sequence assembly may include any suitable methods known in the art including de novo assembly, reference-guided assembly, others, or combinations thereof. In a preferred embodiment, sequence reads are assembled using graph-based alignment methods. See, e.g., U.S. Pub. 2015/0057946 and U.S. Pub. 2015/0056613, both incorporated by reference. Embodiments of a graph and its use are discussed in greater detail below. The result of assembly is a sequence representing the corresponding portion of the original nucleic acid. The contig or consensus sequence or one or more of individual sequence read 2204 may be mapped to a reference graph to find an alignment with an optimal score.

In certain embodiments, each sequence read 2204 is mapped to a reference graph and an alignment is found. As previously noted, alignments of sequence reads to a reference graph may be used as evidence to identify the likelihood of the possible diploid genotypes from an interval in a reference graph.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for encoding genomic data in a computer-readable the method comprising:
   (a) computationally dividing genomic data into a plurality of segments; and
   (b) computationally encoding characters within each of the plurality of segments with a smallest number of bits per character needed to represent all unique characters present in each segment, wherein (i) an identity and number of each character is encoded and (ii) encoding the characters within each of the plurality of segments comprises creating for each segment a segment header and a corresponding data portion, the header comprising information about an alphabet of characters that is encoded by the corresponding data portion,
   and further wherein dividing the genomic data into the plurality of segments comprises:
      scanning the genomic data and keeping track of a number of unique characters scanned; noting positions in the sequence where the number increases to a power of two;
      calculating a compression that would be obtained by dividing the genomic data into one of the plurality of segments at ones of the noted positions that yield the best compression, and
      dividing the genomic data into the plurality of segments at the positions that yield the best compression, and
   (c) storing the encoded characters in the computer-readable medium.

2. The method of claim 1, wherein a first one of the segments uses a different number of bits per character than a second one of the segments.

3. The method of claim 1, wherein, within a segment, every character is encoded using the same number of bits.

4. The method of claim 1, wherein encoding the characters within each of the plurality of segments comprises:
   determining a number N of unique characters in the segment; and
   encoding the segment using X bits per character, where $2^{(x-1)} < N \bullet \leq 2^x$.

5. The method of claim 4, wherein the header comprises at least two bits that indicate a length of the header and a plurality of flag bits, wherein the flag bits identify the alphabet of characters that is encoded by the corresponding data portion.

6. The method of claim 5, wherein the flag bits identify the alphabet using a bitmap to identify included characters.

7. The method of claim 1, wherein the genomic data comprises a directed graph representing at least a portion of a plurality of genomes, and wherein encoding the characters within each of the plurality of segments transforms the directed graph into a sequence of bit, the method further comprising transferring the sequence of bits serially from a computer memory device a computer system to a second computer system.

\* \* \* \* \*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1
cccactaact tcaggatacc a                                                 21

<210> SEQ ID NO 2
<211> LENGTH: 37
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t

<400> SEQUENCE: 2
nnnnnnnnnn nngagatgac gagagagagc taggntt                                37

<210> SEQ ID NO 3
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(12)
<223> OTHER INFORMATION: n is a, c, g, or t

<400> SEQUENCE: 3
nnnnnnnnnn nn                                                           12

<210> SEQ ID NO 4
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 4
gagatgacga gag                                                          13

<210> SEQ ID NO 5
<211> LENGTH: 12
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: (10)..(10)
<223> OTHER INFORMATION: n is a, c, g, or t

<400> SEQUENCE: 5
agagctaggn tt                                                          12

<210> SEQ ID NO 6
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 6 actgactg                                                                8

<210> SEQ ID NO 7
<211> LENGTH: 5
<212> TYPE: DNA
<213> ORGANISM: Artificial Sequence
<220> FEATURE:
<223> OTHER INFORMATION: Synthetic Sequence

<400> SEQUENCE: 7 gactg                                                                   5

<210> SEQ ID NO 8
<211> LENGTH: 5
<212> TYPE: DNA
<213> ORGANISM: Artificial Sequence
<220> FEATURE:
<223> OTHER INFORMATION: Synthetic Sequence

<400> SEQUENCE: 8 tactg                                                                   5
```